(12) United States Patent
Seefeld et al.

(10) Patent No.: US 8,338,434 B2
(45) Date of Patent: Dec. 25, 2012

(54) INHIBITORS OF AKT ACTIVITY

(75) Inventors: Mark Andrew Seefeld, Collegeville, PA (US); Meagan B. Rouse, Collegeville, PA (US)

(73) Assignee: GlaxoSmithKline LLC, Philadelphia, PA (US)

( * ) Notice: Subject to any disclaimer, the term of this patent is extended or adjusted under 35 U.S.C. 154(b) by 446 days.

(21) Appl. No.: 12/593,415

(22) PCT Filed: Mar. 28, 2008

(86) PCT No.: PCT/US2008/058603
§ 371 (c)(1), (2), (4) Date: Sep. 28, 2009

(87) PCT Pub. No.: WO2008/121786
PCT Pub. Date: Oct. 9, 2008

(65) Prior Publication Data
US 2010/0137338 A1    Jun. 3, 2010

Related U.S. Application Data

(60) Provisional application No. 60/908,741, filed on Mar. 29, 2007.

(51) Int. Cl.
*A61K 31/506* (2006.01)
*A61K 31/4427* (2006.01)
*A61K 31/415* (2006.01)
*C07D 401/04* (2006.01)
*C07D 231/12* (2006.01)

(52) U.S. Cl. ........ 514/256; 514/341; 514/406; 544/333; 546/275.4; 548/377.1

(58) Field of Classification Search ........................ None
See application file for complete search history.

(56) References Cited

U.S. PATENT DOCUMENTS

| | | |
|---|---|---|
| 6,875,789 B2 | 4/2005 | Tang et al. |
| 2004/0248853 A1 | 12/2004 | Dyckman et al. |
| 2006/0106027 A1 | 5/2006 | Furet et al. |
| 2006/0270643 A1 | 11/2006 | Chang et al. |

*Primary Examiner* — Kamal Saeed
(74) *Attorney, Agent, or Firm* — Wayne J. Dustman; Edward R. Gimmi

(57) ABSTRACT

Invented are novel pyrazole compounds, the use of such compounds as inhibitors of protein kinase B activity and in the treatment of cancer and arthritis.

3 Claims, No Drawings

INHIBITORS OF AKT ACTIVITY

This application is a 371 of International Application No. PCT/US2008/058603, filed 28 Mar. 2008, which claims the benefit of U.S. Provisional Application No. 60/908,741, filed 29 Mar. 2007.

FIELD OF THE INVENTION

This invention relates to novel pyrazole compounds, the use of such compounds as inhibitors of protein kinase B (hereinafter PKB/Akt, PKB or Akt) activity and in the treatment of cancer and arthritis.

BACKGROUND OF THE INVENTION

The present invention relates to 1H-imidazo[4,5-c]pyridin-2-yl containing compounds that are inhibitors of the activity of one or more of the isoforms of the serine/threonine kinase, Akt (also known as protein kinase B). The present invention also relates to pharmaceutical compositions comprising such compounds and methods of using the instant compounds in the treatment of cancer and arthritis (Liu et al. *Current Opin. Pharmacology* 3:317-22 (2003)).

Apoptosis (programmed cell death) plays essential roles in embryonic development and pathogenesis of various diseases, such as degenerative neuronal diseases, cardiovascular diseases and cancer. Recent work has led to the identification of various pro- and anti-apoptotic gene products that are involved in the regulation or execution of programmed cell death. Expression of anti-apoptotic genes, such as Bcl2 or Bcl-$x_L$, inhibits apoptotic cell death induced by various stimuli. On the other hand, expression of pro-apoptotic genes, such as Bax or Bad, leads to programmed cell death (Adams et al. *Science*, 281:1322-1326 (1998)). The execution of programmed cell death is mediated by caspase-1 related proteinases, including caspase-3, caspase-7, caspase-8 and caspase-9 etc (Thornberry et al. *Science*, 281:1312-1316 (1998)).

The phosphatidylinositol 3'-OH kinase (PI3K)/Akt/PKB pathway appears important for regulating cell survival/cell death (Kulik et al. *Mol. Cell. Biol.* 17:1595-1606 (1997); Franke et al, *Cell*, 88:435-437 (1997); Kauffmann-Zeh et al. *Nature* 385:544-548 (1997) Hemmings *Science*, 275:628-630 (1997); Dudek et al., *Science*, 275:661-665 (1997)). Survival factors, such as platelet derived growth factor (PDGF), nerve growth factor (NGF) and insulin-like growth factor-1 (IGF-I), promote cell survival under various conditions by inducing the activity of PI3K (Kulik et al. 1997, Hemmings 1997). Activated PI3K leads to the production of phosphatidylinositol (3,4,5)-triphosphate (PtdIns (3,4,5)-P3), which in turn binds to, and promotes the activation of, the serine/threonine kinase Akt, which contains a pleckstrin homology (PH)-domain (Franke et al *Cell*, 81:727-736 (1995); Hemmings *Science*, 277:534 (1997); Downward, *Curr. Opin. Cell Biol.* 10:262-267 (1998), Alessi et al., *EMBO J.* 15: 6541-6551 (1996)). Specific inhibitors of PI3K or dominant negative Akt/PKB mutants abolish survival-promoting activities of these growth factors or cytokines. It has been previously disclosed that inhibitors of PI3K (LY294002 or wortmannin) blocked the activation of Akt/PKB by upstream kinases. In addition, introduction of constitutively active PI3K or Akt/PKB mutants promotes cell survival under conditions in which cells normally undergo apoptotic cell death (Kulik et al. 1997, Dudek et al. 1997).

Analysis of Akt levels in human tumors showed that Akt2 is overexpressed in a significant number of ovarian (J. Q. Cheung et al. *Proc. Natl. Acad. Sci. U.S.A.* 89:9267-9271 (1992)) and pancreatic cancers (J. Q. Cheung et al. *Proc. Natl. Acad. Sci. U.S.A.* 93:3636-3641 (1996)). Similarly, Akt3 was found to be overexpressed in breast and prostate cancer cell lines (Nakatani et al. *J. Biol. Chem.* 274:21528-21532 (1999). It was demonstrated that Akt-2 was over-expressed in 12% of ovarian carcinomas and that amplification of Akt was especially frequent in 50% of undifferentiated tumors, suggestion that Akt may also be associated with tumor aggressiveness (Bellacosa, et al., *Int. J. Cancer,* 64, pp. 280-285, 1995). Increased Akt1 kinase activity has been reported in breast, ovarian and prostate cancers (Sun et al. *Am. J. Pathol.* 159: 431-7 (2001)).

The tumor suppressor PTEN, a protein and lipid phosphatase that specifically removes the 3' phosphate of PtdIns (3,4,5)-P3, is a negative regulator of the PI3K/Akt pathway (Li et al. *Science* 275:1943-1947 (1997), Stambolic et al. *Cell* 95:29-39 (1998), Sun et al. *Proc. Natl. Acad. Sci. U.S.A.* 96:6199-6204 (1999)). Germline mutations of PTEN are responsible for human cancer syndromes such as Cowden disease (Liaw et al. *Nature Genetics* 16:64-67 (1997)). PTEN is deleted in a large percentage of human tumors and tumor cell lines without functional PTEN show elevated levels of activated Akt (Li et al. supra, Guldberg et al. *Cancer Research* 57:3660-3663 (1997), Risinger et al. *Cancer Research* 57:4736-4738 (1997)).

These observations demonstrate that the PI3K/Akt pathway plays important roles for regulating cell survival or apoptosis in tumorigenesis.

Three members of the Akt/PKB subfamily of second-messenger regulated serine/threonine protein kinases have been identified and termed Akt1/PKBα, Akt2/PKBβ, and Akt3/PKBγ respectively. The isoforms are homologous, particularly in regions encoding the catalytic domains. Akt/PKBs are activated by phosphorylation events occurring in response to PI3K signaling. PI3K phosphorylates membrane inositol phospholipids, generating the second messengers phosphatidyl-inositol 3,4,5-trisphosphate and phosphatidylinositol 3,4-bisphosphate, which have been shown to bind to the PH domain of Akt/PKB. The current model of Akt/PKB activation proposes recruitment of the enzyme to the membrane by 3'-phosphorylated phosphoinositides, where phosphorylation of the regulatory sites of Akt/PKB by the upstream kinases occurs (B. A. Hemmings, *Science* 275:628-630 (1997); B. A. Hemmings, *Science* 276:534 (1997); J. Downward, *Science* 279:673-674 (1998)).

Phosphorylation of Akt1/PKBα occurs on two regulatory sites, Thr$^{308}$ in the catalytic domain activation loop and on Ser$^{473}$ near the carboxy terminus (D. R. Alessi et al. *EMBO J.* 15:6541-6551 (1996) and R. Meier et al. *J. Biol. Chem.* 272: 30491-30497 (1997)). Equivalent regulatory phosphorylation sites occur in Akt2/PKBβ and Akt3/PKBγ. The upstream kinase, which phosphorylates Akt/PKB at the activation loop site has been cloned and termed 3'-phosphoinositide dependent protein kinase 1 (PDK1). PDK1 phosphorylates not only Akt/PKB, but also p70 ribosomal S6 kinase, p90RSK, serum and glucocorticoid-regulated kinase (SGK), and protein kinase C. The upstream kinase phosphorylating the regulatory site of Akt/PKB near the carboxy terminus has not been identified yet, but recent reports imply a role for the integrin-linked kinase (ILK-1), a serine/threonine protein kinase, or autophosphorylation.

Inhibition of Akt activation and activity can be achieved by inhibiting PI3K with inhibitors such as LY294002 and wortmannin. However, PI3K inhibition has the potential to indiscriminately affect not just all three Akt isozymes but also other PH domain-containing signaling molecules that are dependent on PdtIns(3,4,5)-P3, such as the Tec family of tyrosine kinases. Furthermore, it has been disclosed that Akt can be activated by growth signals that are independent of PI3K.

Alternatively, Akt activity can be inhibited by blocking the activity of the upstream kinase PDK1. The compound UCN-01 is a reported inhibitor of PDK1. *Biochem. J.* 375(2):255 (2003). Again, inhibition of PDK1 would result in inhibition of multiple protein kinases whose activities depend on PDK1, such as atypical PKC isoforms, SGK, and S6 kinases (Williams et al. *Curr. Biol.* 10:439-448 (2000).

Small molecule inhibitors of Akt are useful in the treatment of tumors, especially those with activated Akt (e.g. PTEN null tumors and tumors with ras mutations). PTEN is a critical negative regulator of Akt and its function is lost in many cancers, including breast and prostate carcinomas, glioblastomas, and several cancer syndromes including Bannayan-Zonana syndrome (Maehama, T. et al. *Annual Review of Biochemistry,* 70: 247 (2001)), Cowden disease (Parsons, R.; Simpson, L. *Methods in Molecular Biology* (Totowa, N.J., United States), 222 (*Tumor Suppressor Genes, Volume* 1): 147 (2003)), and Lhermitte-Duclos disease (Backman, S. et al. *Current Opinion in Neurobiology,* 12(5): 516 (2002)). Inhibition of Akt has also been implicated in the treatment of leukemias, (J. C. Byrd, S. Stilgenbauer and I. W. Flinn "Chronic lymphocytic leukemia." Hematology/the Education Program of the American Society of Hematology. American Society of Hematology. Education Program (2004), 163-83). Akt3 is up-regulated in estrogen receptor-deficient breast cancers and androgen-independent prostate cancer cell lines and Akt2 is over-expressed in pancreatic and ovarian carcinomas. Akt1 is amplified in gastric cancers (Staal, *Proc. Natl. Acad. Sci. USA* 84: 5034-7 (1987) and upregulated in breast cancers (Stal et al. *Breast Cancer Res.* 5: R37-R44 (2003)). Therefore a small molecule Akt inhibitor is expected to be useful for the treatment of these types of cancer as well as other types of cancer. Akt inhibitors are also useful in combination with further chemotherapeutic agents.

It is an object of the instant invention to provide novel compounds that are inhibitors of Akt/PKB.

It is also an object of the present invention to provide pharmaceutical compositions that comprise a pharmaceutical carrier and compounds useful in the methods of the invention.

It is also an object of the present invention to provide a method for treating cancer that comprises administering such inhibitors of Akt/PKB activity.

It is also an object of the present invention to provide a method for treating arthritis that comprises administering such inhibitors of Akt/PKB activity.

SUMMARY OF THE INVENTION

This invention relates to novel compounds of Formula (I):

(I)

wherein:
  Q is selected from: phenyl, substituted phenyl, benzyl, and benzyl wherein the aromatic ring is substituted;
  $R^1$ is selected from: hydrogen, trifluoromethyl, hydroxy, —$C_1$-$C_2$alkyl, and halogen;
  L is selected from: nitrogen and —C(H)—;
  P is selected from: nitrogen and —C($R^{40}$)—, where $R^{40}$ is selected from: hydrogen, —$C_1$-$C_4$alkyl, and halogen;
  A is selected from: —C(O)— and —N(H)—;
  B is selected from: —C(O)— and —N(H)—; and
  X, Y and Z are independently selected from: nitrogen, —C(H)—, and —C($R^2$)—, wherein $R^2$ is selected from halogen, trifluoromethyl, hydroxy, and —$C_1$-$C_4$alkyl;
or a pharmaceutically acceptable salt thereof;
  provided:
  A and B are not the same; and
  provided:
  X, Y and Z are not all nitrogen; and
  provided:
  that at most one of P and L are nitrogen.

This invention relates to novel compounds of Formula (II):

(II)

wherein:
  Q is selected from: phenyl, substituted phenyl, benzyl, and benzyl wherein the aromatic ring is substituted;
  $R^1$ is selected from: hydrogen, trifluoromethyl, hydroxy, —$C_1$-$C_2$alkyl, and halogen;
  $R^3$ is selected from: hydrogen, trifluoromethyl, hydroxy, —$C_1$-$C_2$alkyl, and halogen;
  L is selected from: nitrogen and —C(H)—;
  P is selected from: nitrogen and —C($R^{45}$)—, where $R^{45}$ is selected from: hydrogen, —$C_1$-$C_4$alkyl, and halogen;
  A is selected from: —C(O)— and —N(H)—;
  B is selected from: —C(O)— and —N(H)—; and
  X and Y are independently selected from: nitrogen, —C(H)—, and —C($R^2$)—, wherein $R^2$ is selected from halogen, trifluoromethyl, hydroxy, and —$C_1$-$C_4$alkyl;
or pharmaceutically acceptable salt thereof;
  provided:
  A and B are not the same; and
  provided:
  that at most one of P and L are nitrogen.

This invention relates to a method of treating cancer, which comprises administering to a subject in need thereof an effective amount of an Akt/PKB inhibiting compound of Formula (I) or Formula (II).

This invention relates to a method of treating arthritis, which comprises administering to a subject in need thereof an effective amount of an Akt/PKB inhibiting compound of Formula (I) or Formula (II).

The present invention also relates to the discovery that the compounds of Formula (I) and Formula (II) are active as inhibitors of Akt/PKB.

In a further aspect of the invention there is provided novel processes useful in preparing the presently invented Akt/PKB inhibiting compounds.

Included in the present invention are pharmaceutical compositions that comprise a pharmaceutical carrier and compounds useful in the methods of the invention.

Also included in the present invention are methods of co-administering the presently invented Akt/PKB inhibiting compounds with further active ingredients.

DETAILED DESCRIPTION OF THE INVENTION

This invention relates to compounds of Formula (I) and Formula (II) as described above.

The presently invented compounds of Formula (I) and Formula (II) inhibit Akt/PKB activity. In particular, the compounds disclosed herein inhibit each of the three Akt/PKB isoforms.

Included among the presently invented compounds of Formula (I) are compounds of Formula (IA):

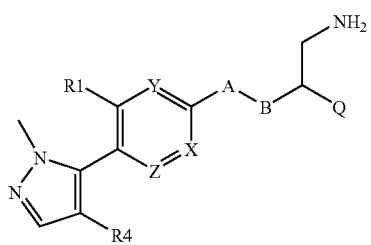

(IA)

wherein:
Q is selected from: phenyl, substituted phenyl, benzyl, and benzyl wherein the aromatic ring is substituted;
$R^1$ is selected from: hydrogen, $-C_1-C_2$alkyl, and halogen;
$R^4$ is selected from: hydrogen, $-C_1-C_4$alkyl, and halogen;
A is selected from: $-C(O)-$ and $-N(H)-$;
B is selected from: $-C(O)-$ and $-N(H)-$; and
X, Y and Z are independently selected from: nitrogen, $-C(H)-$, and $-C(R^2)-$, wherein $R^2$ is selected from halogen and $-C_1-C_4$alkyl;
or a pharmaceutically acceptable salt thereof;
provided:
A and B are not the same; and
provided:
X, Y and Z are not all nitrogen.

Included among the presently invented compounds of Formula (II) are compounds of Formula (IIA):

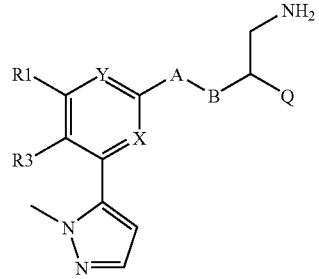

(IIA)

wherein:
Q is selected from: phenyl, substituted phenyl, benzyl, and benzyl wherein the aromatic ring is substituted;
$R^1$ is selected from: hydrogen, $-C_1-C_2$alkyl, and halogen;
$R^3$ is selected from: hydrogen, $-C_1-C_2$alkyl, and halogen;
A is selected from: $-C(O)-$ and $-N(H)-$;
B is selected from: $-C(O)-$ and $-N(H)-$; and
X and Y are independently selected from: nitrogen, $-C(H)-$, and $-C(R^2)-$, wherein $R^2$ is selected from halogen and $-C_1-C_4$alkyl;
or a pharmaceutically acceptable salt thereof;
provided:
A and B are not the same.

Included among the presently invented compounds of Formula (I) and Formula (II) are:
N-[2-amino-1-(phenylmethyl)ethyl]-5-(1-methyl-1H-pyrazol-5-yl)-2-pyridinecarboxamide;
N-[2-amino-1-(phenylmethyl)ethyl]-6-(1-methyl-1H-pyrazol-5-yl)-3-pyridinecarboxamide;
N-(2-amino-1-benzylethyl)-5-(1-methyl-1H-pyrazol-5-yl)pyrimidine-2-carboxamide;
N-[2-amino-1-(phenylmethyl)ethyl]-4-(1-methyl-1H-pyrazol-5-yl)benzamide;
N-[2-amino-1-(phenylmethyl)ethyl]-2-chloro-4-(1-methyl-1H-pyrazol-5-yl)benzamide;
N-[2-amino-1-(phenylmethyl)ethyl]-3-chloro-4-(1-methyl-1H-pyrazol-5-yl)benzamide;
N-[2-amino-1-(phenylmethyl)ethyl]-4-(1-methyl-1H-pyrazol-5-yl)-3-(trifluoromethyl)benzamide;
N-((1S)-2-amino-1-{[2-(trifluoromethyl)phenyl]methyl}ethyl)-5-(1-methyl-1H-pyrazol-5-yl)-2-pyridinecarboxamide;
N-((1S)-2-amino-1-{[2-(trifluoromethyl)phenyl]methyl}ethyl)-3-chloro-4-(1-methyl-1H-pyrazol-5-yl)benzamide;
N-[2-amino-1-(phenylmethyl)ethyl]-4-chloro-5-(1-methyl-1H-pyrazol-5-yl)-2-pyridinecarboxamide;
N-[2-amino-1-(phenylmethyl)ethyl]-4-(1-methyl-1H-pyrazol-5-yl)-2-pyridinecarboxamide;
N-[2-amino-1-(phenylmethyl)ethyl]-6-chloro-5-(1-methyl-1H-pyrazol-5-yl)-2-pyridinecarboxamide;
N-[2-amino-1-(phenylmethyl)ethyl]-6-(1-methyl-1H-pyrazol-5-yl)-2-pyridinecarboxamide;
N-[2-amino-1-(phenylmethyl)ethyl]-5-(1-methyl-1H-pyrazol-5-yl)-3-pyridinecarboxamide;
N-[2-amino-1-(phenylmethyl)ethyl]-2-(1-methyl-1H-pyrazol-5-yl)-4-pyridinecarboxamide;
N-[2-amino-1-(phenylmethyl)ethyl]-3-(1-methyl-1H-pyrazol-5-yl)benzamide;
N-[2-amino-1-(phenylmethyl)ethyl]-3-methyl-4-(1-methyl-1H-pyrazol-5-yl)benzamide;
N-((1S)-2-amino-1-{[2-(trifluoromethyl)phenyl]methyl}ethyl)-3-fluoro-4-(1-methyl-1H-pyrazol-5-yl)benzamide;
N-((1S)-2-amino-1-{[2-(trifluoromethyl)phenyl]methyl}ethyl)-3-methyl-4-(1-methyl-1H-pyrazol-5-yl)benzamide;
N-[2-amino-1-(phenylmethyl)ethyl]-3-hydroxy-4-(1-methyl-1H-pyrazol-5-yl)benzamide;
N-[2-amino-1-(phenylmethyl)ethyl]-3-fluoro-4-(1-methyl-1H-pyrazol-5-yl)benzamide;
N-[2-amino-1-(phenylmethyl)ethyl]-3-chloro-5-(1-methyl-1H-pyrazol-5-yl)benzamide;
N-[2-amino-1-(phenylmethyl)ethyl]-2-chloro-5-(1-methyl-1H-pyrazol-5-yl)benzamide;
N-[2-amino-1-(phenylmethyl)ethyl]-4-chloro-3-(1-methyl-1H-pyrazol-5-yl)benzamide;

N-((1S)-2-amino-1-{[2-(trifluoromethyl)phenyl]
  methyl}ethyl)-4-chloro-5-(1-methyl-1H-pyrazol-5-yl)-2-
  pyridinecarboxamide;
N-((1S)-2-amino-1-{[2-(trifluoromethyl)phenyl]
  methyl}ethyl)-4-chloro-3-(1-methyl-1H-pyrazol-5-yl)
  benzamide;
N-[2-amino-1-(phenylmethyl)ethyl]-4-(4-chloro-1-methyl-
  1H-pyrazol-5-yl)-3-fluorobenzamide;
N-[2-amino-1-(phenylmethyl)ethyl]-3-chloro-4-(4-chloro-
  1-methyl-1H-pyrazol-5-yl)benzamide;
N-((1S)-2-amino-1-{[2-(trifluoromethyl)phenyl]
  methyl}ethyl)-3-fluoro-4-(4-chloro-1-methyl-1H-pyra-
  zol-5-yl)benzamide;
N-((1S)-2-amino-1-{[2-(trifluoromethyl)phenyl]
  methyl}ethyl)-3-chloro-4-(4-chloro-1-methyl-1H-pyra-
  zol-5-yl)benzamide;
N-[2-amino-1-(phenylmethyl)ethyl]-3-bromo-4-(1-methyl-
  1H-pyrazol-5-yl)benzamide;
N-((1S)-2-amino-1-{[2-(trifluoromethyl)phenyl]
  methyl}ethyl)-3-bromo-4-(1-methyl-1H-pyrazol-5-yl)
  benzamide;
3-amino-N-[3-chloro-4-(1-methyl-1H-pyrazol-5-yl)phe-
  nyl]-2-phenylpropanamide;
3-amino-N-[3-chloro-4-(1-methyl-1H-pyrazol-5-yl)phe-
  nyl]-2-(phenylmethyl)propanamide;
3-amino-N-[3-(1-methyl-1H-pyrazol-5-yl)phenyl]-2-(phe-
  nylmethyl)propanamide;
N-((1S)-2-amino-1-{[2-(trifluoromethyl)phenyl]
  methyl}ethyl)-4-(1-methyl-1H-1,2,4-triazol-5-yl)benza-
  mide;
N-[(1S)-2-amino-1-(phenylmethyl)ethyl]-4-(1-methyl-1H-
  1,2,4-triazol-5-yl)benzamide;
N-{(1S)-2-amino-1-[(3-fluorophenyl)methyl]ethyl}-4-(1-
  methyl-1H-1,2,4-triazol-5-yl)benzamide;
N-((1S)-2-amino-1-{[2-(trifluoromethyl)phenyl]
  methyl}ethyl)-3-chloro-4-(1-methyl-1H-1,2,4-triazol-5-
  yl)benzamide;
N-{(1S)-2-amino-1-[(3-fluorophenyl)methyl]ethyl}-3-
  chloro-4-(1-methyl-1H-1,2,4-triazol-5-yl)benzamide;
N-[(1S)-2-amino-1-(phenylmethyl)ethyl]-3-chloro-4-(1-
  methyl-1H-1,2,4-triazol-5-yl)benzamide;
N-((1S)-2-amino-1-{[2-(trifluoromethyl)phenyl]
  methyl}ethyl)-4-(1-methyl-1H-1,2,3-triazol-5-yl)benza-
  mide;
N-((1S)-2-amino-1-{[2-(trifluoromethyl)phenyl]
  methyl}ethyl)-4-(4-chloro-1-methyl-1H-1,2,3-triazol-5-
  yl)benzamide;
N-[(1S)-2-amino-1-(phenylmethyl)ethyl]-4-(4-chloro-1-
  methyl-1H-1,2,3-triazol-5-yl)benzamide;
N-{(1S)-2-amino-1-[(3-fluorophenyl)methyl]ethyl}-4-(4-
  chloro-1-methyl-1H-1,2,3-triazol-5-yl)benzamide;
N-[(1S)-2-amino-1-(phenylmethyl)ethyl]-4-(1-methyl-1H-
  1,2,3-triazol-5-yl)benzamide; and
N-{(1S)-2-amino-1-[(3-fluorophenyl)methyl]ethyl}-4-(1-
  methyl-1H-1,2,3-triazol-5-yl)benzamide;
or a pharmaceutically acceptable salt thereof.

Compounds of Formula (I) and Formula (II) are included in the pharmaceutical compositions of the invention and used in the methods of the invention.

Certain of the compounds described herein may contain one or more chiral atoms, or may otherwise be capable of existing as two enantiomers. Accordingly, the compounds of this invention include mixtures of enantiomers as well as purified enantiomers or enantiomerically enriched mixtures. Also, it is understood that all tautomers and mixtures of tautomers are included within the scope of the compounds of Formula (I) and Formula (II).

Certain compounds described herein may form a solvate which is understood to be a complex of variable stoichiometry formed by a solute (in this invention, a compound of Formula (I) or a salt thereof, or a compound of Formula (II) or a salt thereof) and a solvent. Such solvents for the purpose of the invention may not interfere with the biological activity of the solute. Examples of suitable solvents include, but are not limited to, water, methanol, ethanol and acetic acid. Preferably the solvent used is a pharmaceutically acceptable solvent. Examples of suitable pharmaceutically acceptable solvents include, without limitation, water, ethanol and acetic acid.

By the term "aryl", and derivatives thereof, used alone or as part of a larger moiety as in "—$(CH_2)_m$aryl" as used herein, unless otherwise defined, is meant monocyclic, bicyclic, and tricyclic ring systems having a total of five to fourteen ring members, wherein at least one ring system is aromatic and wherein each ring in the system contains 3 to 7 members, such as phenyl, naphthalene, tetrahydronaphthalene and biphenyl.

By the term "$C_5$-$C_{12}$aryl", used alone or as part of a larger moiety as in "—$(CH_2)_m C_5$-$C_{12}$aryl", as used herein, is meant an aromatic group selected from: phenyl, naphthalene, tehrahydronaphthanlene and biphenyl.

The term "substituted" as used herein, unless otherwise defined, is meant that the subject chemical moiety has from one to five substituents, suitably from one to three substituents, selected from the group consisting of: —$CO_2R^{20}$, $C_1$-$C_4$alkyl, hydroxy$C_1$-$C_4$alkyl, $C_1$-$C_4$alkyloxy, amino, $C_1$-$C_4$alkylamino, amino$C_1$-$C_4$alkyl, di$C_1$-$C_4$alkylamino, hydroxy, nitro, tetrazole, cyano, oxo, halogen and trifluoromethyl, where $R^{20}$ is selected form hydrogen, $C_1$-$C_4$alkyl, and trifluoromethyl.

Suitably, the term "substituted" as used herein is meant that the subject chemical moiety has from one to three substituents, selected from the group consisting of: $C_1$-$C_4$alkyl, hydroxy$C_1$-$C_4$alkyl, $C_1$-$C_4$alkyloxy, amino, $C_1$-$C_4$alkylamino, amino$C_1$-$C_4$alkyl, hydroxy, tetrazole, halogen and trifluoromethyl.

Suitably, the term "substituted" as used herein is meant that the subject chemical moiety has one substituent, selected from the group consisting of: fluoride and trifluoromethyl.

By the term "heteroatom" as used herein is meant oxygen, nitrogen or sulfur.

By the term "halogen" as used herein is meant a substituent selected from bromide, iodide, chloride and fluoride.

By the term "alkyl" and derivatives thereof and in all carbon chains as used herein, including alkyl chains defined by the term "—$(CH_2)_n$", "—$(CH_2)_m$" and the like, is meant a linear or branched, saturated or unsaturated hydrocarbon chain, and unless otherwise defined, the carbon chain will contain from 1 to 12 carbon atoms. Examples of alkyl as used herein include: —$CH_3$, —$CH_2$—$CH_3$, —$CH_2$—$CH_2$—$CH_3$, —$CH(CH_3)_2$, —$CH_2$—$CH_2$—$C(CH_3)_3$, —$C\equiv C$—$C(CH_3)_3$, —$C(CH_3)_3$, —$(CH_2)_3$—$CH_3$, —$CH_2$—$CH(CH_3)_2$, —$CH(CH_3)$—$CH_2$—$CH_3$, —$CH=CH_2$, and —$C\equiv C$—$CH_3$.

By the term "treating" and derivatives thereof as used herein, is meant prophylatic and therapeutic therapy. Prophylactic therapy is appropriate, for example, when a subject is considered at high risk for developing cancer, or when a subject has been exposed to a carcinogen.

By the phrases "to a therapeutic extent", "treating" and "therapeutically effective amount" and derivatives thereof as used herein, unless otherwise defined, is meant that amount of a drug or pharmaceutical agent that will elicit the biological or medical response of a tissue, system, animal or human that is being sought, for instance, by a researcher or clinician. Furthermore, the term "therapeutically effective amount" means any amount which, as compared to a corresponding subject who has not received such amount, results in improved treatment, healing, prevention, lessening in severity or amelioration of specified cancers.

The pharmaceutically acceptable salts of the compounds of the invention are readily prepared by those of skill in the art.

Compounds of Formula (I) and Formula (II) are included in the pharmaceutical compositions of the invention and used in the methods of the invention. Where a —COOH or —OH group is present, pharmaceutically acceptable esters can be employed, for example methyl, ethyl, pivaloyloxymethyl, and the like for —COOH, and acetate maleate and the like for —OH, and those esters known in the art for modifying solubility or hydrolysis characteristics, for use as sustained release or prodrug formulations.

The compounds of Formula (I) and Formula (II) are prepared as shown in Schemes 1 to 3 below, or by analogous methods. All of the starting materials are commercially available, readily made from commercially available starting materials by those of skill in the art or prepared according to literature reports unless otherwise noted in the experimental section.

Scheme 1

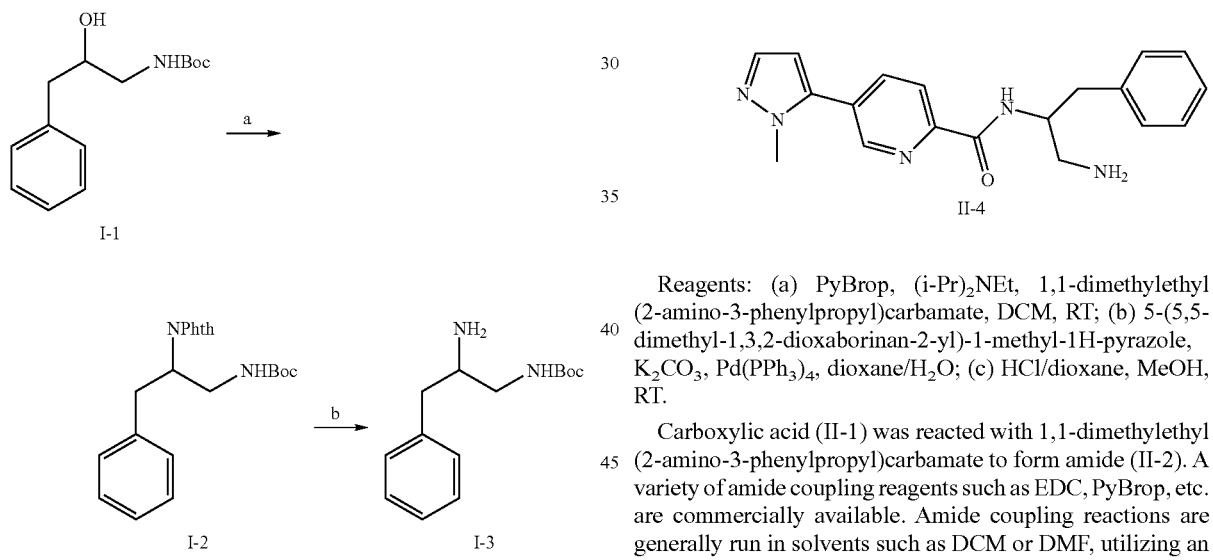

Reagents: (a) Phthalimide, PPh$_3$, DEAD, THF, RT; (b) NH$_2$NH$_2$, MeOH, 50° C.

Amino alcohol (I-1) was reacted under Mitsunobu conditions to provide the differentially protected diamine (I-2). Mitsunobu reactions are well know to those skilled in the art of organic synthesis. Methods and reaction conditions for such transformations are discussed in *Synthesis* 1981, 1-28. Selective deprotection of the phthalimide group of (I-2) using a nucleophilic amine such as hydrazine or methyl amine in a polar solvent such as methanol, afforded amine (I-3). Many different protecting groups are available to one skilled in the art and can be used here as long as they do not interfere with the processes listed herein. Methods for the protection of amines are described in standard reference volumes, such as Greene "Protective Groups in Organic Synthesis" (published by Wiley-Interscience).

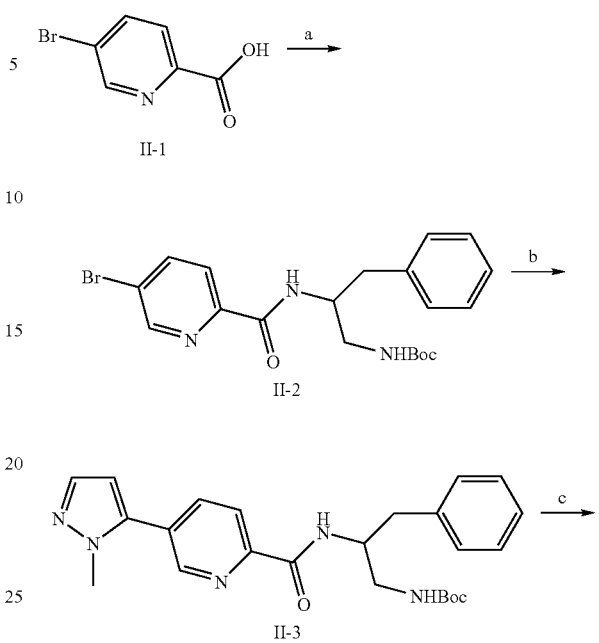

Reagents: (a) PyBrop, (i-Pr)$_2$NEt, 1,1-dimethylethyl (2-amino-3-phenylpropyl)carbamate, DCM, RT; (b) 5-(5,5-dimethyl-1,3,2-dioxaborinan-2-yl)-1-methyl-1H-pyrazole, K$_2$CO$_3$, Pd(PPh$_3$)$_4$, dioxane/H$_2$O; (c) HCl/dioxane, MeOH, RT.

Carboxylic acid (II-1) was reacted with 1,1-dimethylethyl (2-amino-3-phenylpropyl)carbamate to form amide (II-2). A variety of amide coupling reagents such as EDC, PyBrop, etc. are commercially available. Amide coupling reactions are generally run in solvents such as DCM or DMF, utilizing an organic base like Et$_3$N or (i-Pr)$_2$NEt. Bromide (II-2) was coupled with 5-(5,5-dimethyl-1,3,2-dioxaborinan-2-yl)-1-methyl-1H-pyrazole using a Suzuki coupling procedure. Suzuki-like couplings are typically run using a palladium(0) catalyst such as Pd(PPh$_3$)$_4$ with an inorganic base, for example K$_2$CO$_3$, Na$_2$CO$_3$ or K$_3$PO$_4$, in an aqueous mixture containing ethereal solvents such as DME, dioxane, or THF. Methods for palladium-mediated couplings are described in standard reference volumes, such as Schlosser "Organometallics in Synthesis" (published by Wiley and sons). Acidic treatment of II-3 with HCl or TFA to remove the Boc protecting group produced amine (II-4). Many different protecting groups are available to one skilled in the art and can be used here as long as they do not interfere with the processes listed herein. Methods for the protection of amines are described in standard reference volumes, such as Greene "Protective Groups in Organic Synthesis" (published by Wiley-Interscience).

Scheme 3

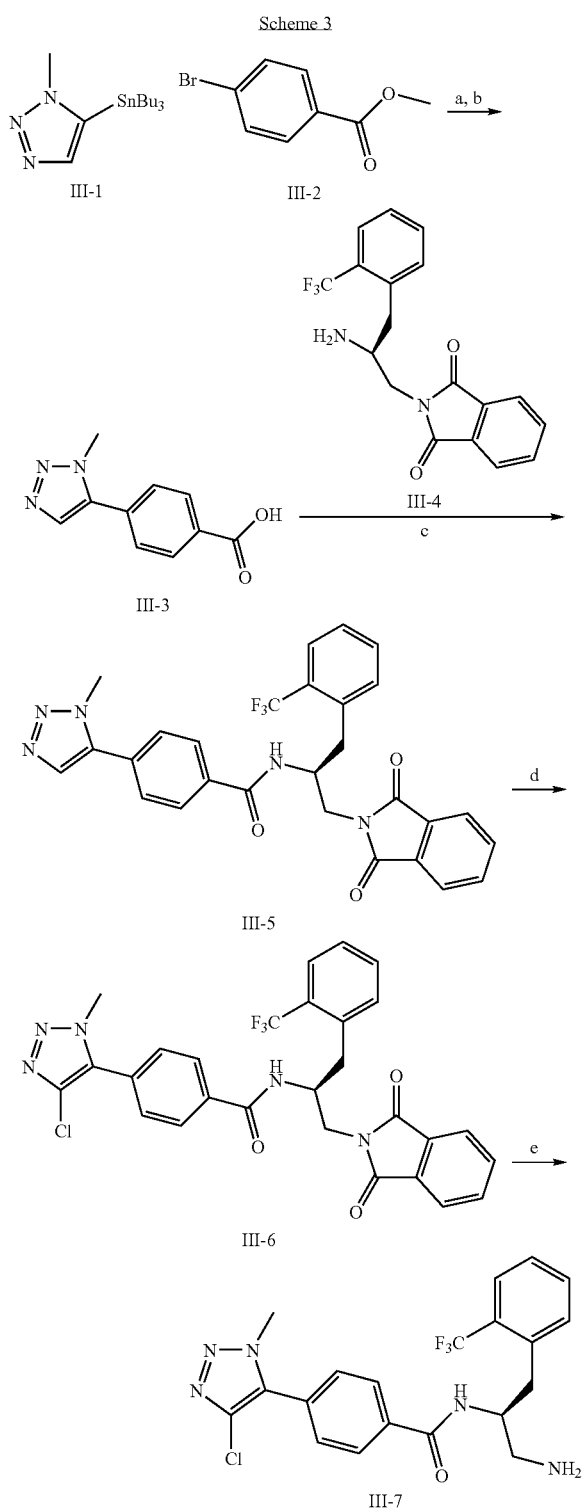

Reagents: (a) Pd(PPh₃)₂Cl₂, Et₃N, toluene, 100° C.; (b) 2N NaOH, THF; (c) PyBrop, (i-Pr)₂NEt, DCM, RT; (d) NCS, DMF, 50° C.; (e) hydrazine hydrate, MeOH/DCM.

1-Methyl-5-(tributylstannanyl)-1H-1,2,3-triazole (III-I) was coupled with methyl 4-bromobenzoate (III-2) using a Stille coupling procedure. Stille-like couplings are typically catalyzed by a palladium(0) catalyst such as Pd(PPh₃)₄ with an organic base, for example Et₃N, in toluene, DMF and dioxane. Methods for palladium-mediated couplings are described in standard reference volumes, such as Schlosser "Organometallics in Synthesis" (published by Wiley and sons). Carboxylic acid (III-3) was reacted with 2-{(2S)-2-amino-3-[2-(trifluoromethyl)phenyl]propyl}-1H-isoindole-1,3(2H)-dione to form amide (III-5). A variety of amide coupling reagents such as EDC, PyBrop, etc. are commercially available. Amide coupling reactions are generally run in solvents such as DCM or DMF, utilizing an organic base like Et₃N or (i-Pr)₂NEt. Chlorination of the triazole was realized with NCS in DMF. The treatment of III-6 with hydrazine hydrate to remove the phthilamide protecting group produced amine (III-7).

By the term "co-administering" and derivatives thereof as used herein is meant either simultaneous administration or any manner of separate sequential administration of an AKT inhibiting compound, as described herein, and a further active ingredient or ingredients, known to be useful in the treatment of cancer, including chemotherapy and radiation treatment, or to be useful in the treatment of arthritis. The term further active ingredient or ingredients, as used herein, includes any compound or therapeutic agent known to or that demonstrates advantageous properties when administered to a patient in need of treatment for cancer or arthritis. Preferably, if the administration is not simultaneous, the compounds are administered in a close time proximity to each other. Furthermore, it does not matter if the compounds are administered in the same dosage form, e.g. one compound may be administered topically and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the presently invented AKT inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the G₂/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)-N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide. 1998) related to the duration of dosing above a threshold concentration (50 nM) (Kearns, C. M. et. al., Seminars in Oncology, 3(6) p. 16-23, 1995).

Docetaxel, (2R,3S)-N-carboxy-3-phenylisoserine,N-tert-butyl ester, 13-ester with 5β-20-epoxy-1,2α,4,7β,10β,13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R-(R*,R*)-2,3-dihydroxybutanedioate (1:2)(salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine [1,1-cyclobutane-dicarboxylate(2)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-trihydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific antineoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mecaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino)carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of formula A following, currently under development, including the racemic mixture (R,S) form as well as the R and S enantiomers:

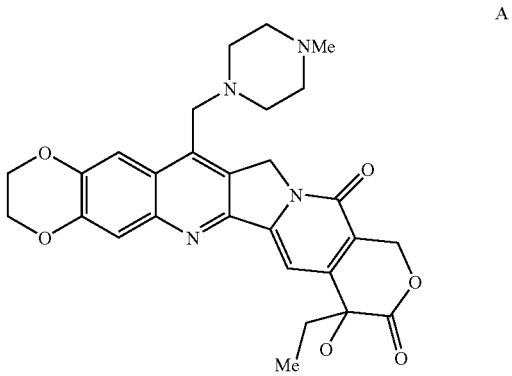

known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent Application No. Ser. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/

SH3domain blockers, serine/threonine kinases, phosphotidyl inositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and anti-sense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 February 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S. and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-Iacaci, L., et al, Int. J. Cancer (2000), 88(1), 44-52.

Inhibitors of Phosphotidyl inositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kniases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) are also useful in combination with the compounds disclosed herein. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of Formula (I) and Formula (II). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

In one embodiment, the cancer treatment method of the claimed invention includes the co-administration a compound of Formula (I) or Formula (II) and/or a pharmaceutically acceptable salt, hydrate, solvate or pro-drug thereof and at least one anti-neoplastic agent, such as one selected from the group consisting of anti-microtubule agents, platinum coordination complexes, alkylating agents, antibiotic agents, topoisomerase II inhibitors, antimetabolites, topoisomerase I inhibitors, hormones and hormonal analogues, signal transduction pathway inhibitors, non-receptor tyrosine kinase angiogenesis inhibitors, immunotherapeutic agents, proapoptotic agents, and cell cycle signaling inhibitors.

Because the pharmaceutically active compounds of the present invention are active as AKT inhibitors they exhibit therapeutic utility in treating cancer and arthritis.

The present invention therefore provides a method of treating cancer in a mammal, including a human, including wherein the cancer is selected from: brain (gliomas), glioblastomas, leukemias, Bannayan-Zonana syndrome, Cowden disease, Lhermitte-Duclos disease, breast, inflammatory breast cancer, Wilm's tumor, Ewing's sarcoma, Rhabdomyosarcoma, ependymoma, medulloblastoma, colon, head and neck, kidney, lung, liver, melanoma, ovarian, pancreatic, prostate, sarcoma, osteosarcoma, giant cell tumor of bone, thyroid, Lymphoblastic T cell leukemia, Chronic myelogenous leukemia, Chronic lymphocytic leukemia, Hairy-cell leukemia, acute lymphoblastic leukemia, acute myelogenous leukemia, Chronic neutrophilic leukemia, Acute lymphoblastic T cell leukemia, Plasmacytoma, Immunoblastic large cell leukemia, Mantle cell leukemia, Multiple myeloma Megakaryoblastic leukemia, multiple myeloma, Acute megakaryocytic leukemia, promyelocytic leukemia, Erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, lung cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer, which comprises the administration an effective amount of a presently invented AKT inhibiting compound.

Suitably, the present invention relates to a method for treating a cancer selected from brain (gliomas), glioblastomas, leukemias, Bannayan-Zonana syndrome, Cowden disease, Lhermitte-Duclos disease, breast, colon, head and neck, kidney, lung, liver, melanoma, ovarian, pancreatic, prostate, sarcoma and thyroid.

Suitably, the present invention relates to a method for treating a cancer selected from breast, ovarian, pancreatic and prostate.

Isolation and Purification of His-Tagged AKT1 (aa 136-480)

Insect cells expressing His-tagged AKT1 (aa 136-480) were lysed in 25 mM HEPES, 100 mM NaCl, 20 mM imidazole; pH 7.5 using a polytron (5 mLs lysis buffer/g cells). Cell debris was removed by centrifuging at 28,000×g for 30 minutes. The supernatant was filtered through a 4.5-micron filter then loaded onto a nickel-chelating column pre-equilibrated with lysis buffer. The column was washed with 5 column volumes (CV) of lysis buffer then with 5 CV of 20% buffer B, where buffer B is 25 mM HEPES, 100 mM NaCl, 300 mM imidazole; pH 7.5. His-tagged AKT1 (aa 136-480) was eluted with a 20-100% linear gradient of buffer B over 10 CV. His-tagged AKT1 (136-480) eluting fractions were pooled and diluted 3-fold with buffer C, where buffer C is 25 mM HEPES, pH 7.5. The sample was then chromatographed over a Q-Sepharose HP column pre-equilibrated with buffer C. The column was washed with 5 CV of buffer C then step eluted with 5 CV 10% D, 5 CV 20% D, 5 CV 30% D, 5 CV 50% D and 5 CV of 100% D; where buffer D is 25 mM HEPES, 1000 mM NaCl; pH 7.5. His-tagged AKT1 (aa 136-480) containing fractions were pooled and concentrated in a 10-kDa molecular weight cutoff concentrator. His-tagged AKT1 (aa 136-480) was chromatographed over a Superdex 75 gel filtration column pre-equilibrated with 25 mM HEPES, 200 mM NaCl, 1 mM DTT; pH 7.5. His-tagged AKT1 (aa 136-480) fractions were examined using SDS-PAGE and mass spec. The protein was pooled, concentrated and frozen at −80 C.

His-tagged AKT2 (aa 138-481) and His-tagged AKT3 (aa 135-479) were isolated and purified in a similar fashion.

His-Tagged AKT Enzyme Assay

Compounds of the present invention were tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. AKT 1, 2 and 3 are also commercially available from Upstate USA, Inc. The method measures the ability of the isolated enzyme to catalyze the transfer of the gamma-phosphate from ATP onto the serine residue of a biotinylated synthetic peptide SEQ. ID NO: 1 (Biotin-ahx-ARKRERAYSFGHHA-amide). Substrate phosphorylation was detected by the following procedure:

Assays were performed in 384well U-bottom white plates. 10 nM activated AKT enzyme was incubated for 40 minutes at room temperature in an assay volume of 20 ul containing 50 mM MOPS, pH 7.5, 20 mM MgCl$_2$, 4 uM ATP, 8 uM peptide, 0.04 uCi [g-$^{33}$P] ATP/well, 1 mM CHAPS, 2 mM DTT, and 1 ul of test compound in 100% DMSO. The reaction was stopped by the addition of 50 ul SPA bead mix (Dulbecco's PBS without Mg$^{2+}$ and Ca$^{2+}$, 0.1% Triton X-100, 5 mM EDTA, 50 uM ATP, 2.5 mg/ml Streptavidin-coated SPA beads.) The plate was sealed, the beads were allowed to settle overnight, and then the plate was counted in a Packard Topcount Microplate Scintillation Counter (Packard Instrument Co., Meriden, Conn.).

The data for dose responses were plotted as % Control calculated with the data reduction formula 100*(U1−C2)/(C1−C2) versus concentration of compound where U is the unknown value, C1 is the average control value obtained for DMSO, and C2 is the average control value obtained for 0.1M EDTA. Data are fitted to the curve described by: y=((Vmax*x)/(K+x)) where Vmax is the upper asymptote and K is the IC50.

Cloning of Full-Length Human (FL) AKT1:

Full-length human AKT1 gene was amplified by PCR from a plasmid containing myristylated-AKT1-ER (gift from Robert T. Abraham, Duke University under MTA, described in Klippel et al. in Molecular and Cellular Biology 1998 Volume 18 p. 5699) using the 5' primer: SEQ. ID NO: 2 5' TATATAG-GATCCATGAGCGACGTGGC 3' and the 3' primer: SEQ. ID NO: 3 AAATTTCTCGAGTCAGGCCGTGCTGCTGG 3'. The 5' primer included a BamHI site and the 3'primer included an XhoI site for cloning purposes. The resultant PCR product was subcloned in pcDNA3 as a BamHI/XhoI fragment. A mutation in the sequence (TGC) coding for a Cysteine$^{25}$ was converted to the wild-type AKT1 sequence (CGC) coding for an Arginine$^{25}$ by site-directed mutagenesis using the QuikChange® Site Directed Mutagenesis Kit (Stratagene). The AKT1 mutagenic primer: SEQ. ID NO: 4 5' ACCTGGCGGCCACGCTACTTCCTCC and selection primer: SEQ. ID NO: 5 5' CTCGAGCATGCAACTA-GAGGGCC (designed to destroy an XbaI site in the multiple cloning site of pcDNA3) were used according to manufacturer's suggestions. For expression/purification purposes, AKT1 was isolated as a BamHI/XhoI fragment and cloned into the BamHI/XhoI sites of pFastbacHTb (Invitrogen).

Expression of FL Human AKT1:

Expression was done using the BAC-to-BAC Baculovirus Expression System from Invitrogen (catalog #10359-016). Briefly 1) the cDNA was transferred from the FastBac vector into bacmid DNA, 2) the bacmid DNA was isolated and used to transfect Sf9 insect cells, 3) the virus was produced in Sf9 cells, 4) T. ni cells were infected with this virus and sent for purification.

Purification of FL Human AKT1:

For the purification of full-length AKT1, 130 g sf9 cells (batch #41646W02) were resuspended in lysis buffer (buffer A, 1 L, pH 7.5) containing 25 mM HEPES, 100 mM NaCl, and 20 mM imidazole. The cell lysis was carried out by Avestin (2 passes at 15K-20K psi). Cell debris was removed by centrifuging at 16K rpm for 1 hour and the supernatant was batch bound to 10 ml Nickel Sepharose HP beads at 4 C for over night. The beads were then transferred to column and the bound material was eluted with buffer B (25 mM HEPES, 100 mM NaCl, 300 mM imidazole, pH 7.5). AKT eluting fractions were pooled and diluted 3 fold using buffer C (25 mM HEPES, 5 mM DTT; pH 7.5). The sample was filtered and chromatographed over a 10 mL Q-HP column pre-equilibrated with buffer C at 2 mL/min.

The Q-HP column was washed with 3 column volume (CV) of buffer C, then step eluted with 5 CV 10% D, 5 CV 20% D, 5 CV 30% D, 5 CV 50% D and 5 CV of 100% D; where buffer D is 25 mM HEPES, 1000 mM NaCl, 5 mM DTT; pH 7.5. 5 mL fractions collected. AKT containing fractions were pooled and concentrated to 5 ml. The protein was next loaded to a 120 ml Superdex 75 sizing column that was pre-equilibrated with 25 mM HEPES, 200 mM NaCl, 5 mM DTT; pH 7.5. 2.5 mL fractions were collected.

AKT 1 eluting fractions were pooled, aliquoted (1 ml) and stored at −80 C. Mass spec and SDS-PAGE analysis were used to confirm purity and identity of the purified full-length AKT1.

Full-length (FL) AKT2 and (FL) AKT3 were isolated and purified in a similar fashion.

Full-Length AKT Enzyme Assay

Compounds of the present invention were tested for AKT 1, 2, and 3 protein serine kinase inhibitory activity in substrate phosphorylation assays. This assay examines the ability of small molecule organic compounds to inhibit the serine phosphorylation of a peptide substrate. The substrate phosphorylation assays use the catalytic domains of AKT 1, 2, or 3. The method measures the ability of the isolated enzyme to catalyze the transfer of the gamma-phosphate from ATP onto the serine residue of a biotinylated synthetic peptide SEQ. ID NO: 1 (Biotin-ahx-ARKRERAYSFGHHA-amide). Substrate phosphorylation was detected by the following procedure.

Assays were performed in 384well U-bottom white plates. 10 nM activated AKT enzyme was incubated for 40 minutes at room temperature in an assay volume of 20 ul containing 50 mM MOPS, pH 7.5, 20 mM MgCl2, 4 uM ATP, 8 uM peptide, 0.04 uCi [g-33P] ATP/well, 1 mM CHAPS, 2 mM DTT, and 1 ul of test compound in 100% DMSO. The reaction was stopped by the addition of 50 ul SPA bead mix (Dulbecco's PBS without Mg$^{2+}$ and Ca$^{2+}$, 0.1% Triton X-100, 5 mM EDTA, 50 uM ATP, 2.5 mg/ml Streptavidin-coated SPA beads.) The plate was sealed, the beads were allowed to settle overnight, and then the plate was counted in a Packard Topcount Microplate Scintillation Counter (Packard Instrument Co., Meriden, Conn.). The data for dose responses were plotted as % Control calculated with the data reduction formula 100*(U1−C2)/(C1−C2) versus concentration of compound where U is the unknown value, C1 is the average control value obtained for DMSO, and C2 is the average control value obtained for 0.1M EDTA. Data are fitted to the curve described by: y=((Vmax*x)/(K+x)) where Vmax is the upper asymptote and K is the IC50.

Compounds of the invention are tested for activity against AKT1, AKT2, and AKT3 in one or more of the above assays.

The compounds of the Examples were tested generally according to the above AKT enzyme assays and in at least one experimental run exhibited a pIC50 value: ≧5.5 against full length AKT1.

The compound of Example 2 was tested generally according to the above AKT enzyme assays and in at least one experimental run exhibited a pIC50 value of 8.0 against full length AKT1.

In the above data, pIC50 is defined as −log(IC50) where the IC50 value is expressed in molar units.

The pharmaceutically active compounds within the scope of this invention are useful as AKT inhibitors in mammals, particularly humans, in need thereof.

The present invention therefore provides a method of treating cancer, arthritis and other conditions requiring AKT inhibition, which comprises administering an effective amount of a compound of Formula (I) or Formula (II) or a pharmaceutically acceptable salt, hydrate, solvate or pro-drug thereof. The compounds of Formula (I) and Formula (II) also provide for a method of treating the above indicated disease states because of their demonstrated ability to act as Akt inhibitors. The drug may be administered to a patient in need thereof by any conventional route of administration, including, but not limited to, intravenous, intramuscular, oral, subcutaneous, intradermal, and parenteral.

The pharmaceutically active compounds of the present invention are incorporated into convenient dosage forms such as capsules, tablets, or injectable preparations. Solid or liquid pharmaceutical carriers are employed. Solid carriers include, starch, lactose, calcium sulfate dihydrate, terra alba, sucrose, talc, gelatin, agar, pectin, acacia, magnesium stearate, and stearic acid. Liquid carriers include syrup, peanut oil, olive oil, saline, and water. Similarly, the carrier may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will, for example, be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the presently invented pharmaceutically active compounds in a pharmaceutical dosage unit as described above will be an efficacious, nontoxic quantity preferably selected from the range of 0.001-100 mg/kg of active compound, preferably 0.001-50 mg/kg. When treating a human patient in need of an Akt inhibitor, the selected dose is administered preferably from 1-6 times daily, orally or parenterally. Preferred forms of parenteral administration include topically, rectally, transdermally, by injection and continuously by infusion. Oral and/or parenteral dosage units for human administration preferably contain from 0.05 to 3500 mg of active compound.

Optimal dosages to be administered may be readily determined by those skilled in the art, and will vary with the particular Akt inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing Akt inhibitory activity in mammals, including humans, comprises administering to a subject in need of such activity an effective Akt inhibiting amount of a pharmaceutically active compound of the present invention.

The invention also provides for the use of a compound of Formula (I) or Formula (II) in the manufacture of a medicament for use as an Akt inhibitor.

The invention also provides for the use of a compound of Formula (I) or Formula (II) in the manufacture of a medicament for use in therapy.

The invention also provides for the use of a compound of Formula (I) or Formula (II) in the manufacture of a medicament for use in treating cancer.

The invention also provides for the use of a compound of Formula (I) or Formula (II) in the manufacture of a medicament for use in treating arthritis.

The invention also provides for a pharmaceutical composition for use as an Akt inhibitor which comprises a compound of Formula (I) or Formula (II) and a pharmaceutically acceptable carrier.

The invention also provides for a pharmaceutical composition for use in the treatment of cancer which comprises a compound of Formula (I) or Formula (II) and a pharmaceutically acceptable carrier.

The invention also provides for a pharmaceutical composition for use in treating arthritis which comprises a compound of Formula (I) or Formula (II) and a pharmaceutically acceptable carrier.

No unacceptable toxicological effects are expected when compounds of the invention are administered in accordance with the present invention.

In addition, the pharmaceutically active compounds of the present invention can be co-administered with further active ingredients, such as other compounds known to treat cancer or arthritis, or compounds known to have utility when used in combination with an Akt inhibitor.

Without further elaboration, it is believed that one skilled in the art can, using the preceding description, utilize the present invention to its fullest extent. The following Examples are, therefore, to be construed as merely illustrative and not a limitation of the scope of the present invention in any way.

Experimental Details

The compounds of Examples 1 to 47 are readily made according to Schemes 1 to 3 or by analogous methods.

Preparation 1

Preparation of
1,1-dimethylethyl(2-amino-2-phenylethyl)carbamate

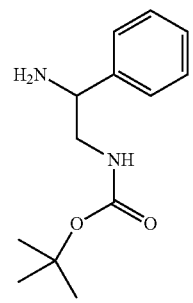

a) 1,1-dimethylethyl(2-hydroxy-2-phenylethyl)carbamate

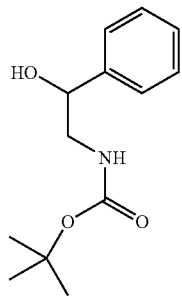

To a solution of 2-amino-1-phenylethanol (5 g, 36.4 mmol) in THF (182 mL) at 25° C. was added Boc₂O (8.7 g, 40.1 mmol) in one portion. After 0.5 h, the solution was concentrated and the residue used directly without further purification: LC-MS (ES) m/z=238 (M+H)⁺.

b) 1,1-dimethylethyl[2-(1,3-dioxo-1,3-dihydro-2H-isoindol-2-yl)-2-phenylethyl]carbamate

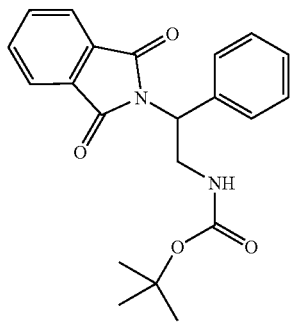

To a solution of 1,1-dimethylethyl(2-hydroxy-2-phenylethyl)carbamate (2 g, 8.44 mmol), phthalimide (1 g, 7.03 mmol) and triphenylphosphine (2.76 g, 10.5 mmol) in THF (35 mL) at 25° C. was added DEAD (1.7 mL, 10.5 mmol) dropwise. After 0.5 h, the solution was concentrated and purified via column chromatography (silica, 15% EtOAc in hexanes) affording the title compound (2 g, 80%) as a white foam: LC-MS (ES) m/z=367 (M+H)⁺.

c) 1,1-dimethylethyl(2-amino-2-phenylethyl)carbamate

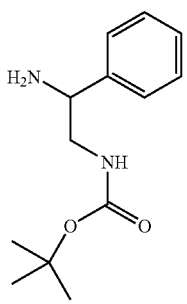

A solution of 1,1-dimethylethyl[2-(1,3-dioxo-1,3-dihydro-2H-isoindol-2-yl)-2-phenylethyl]carbamate (2 g, 5.46 mmol) and either MeNH₂ (40 wt % in H₂O, 10 eq.) or NH₂NH₂ (10 eq.) in MeOH (0.5M, 10 mL) was heated to 60° C. in a sealed tube. After 12 h, the solution was concentrated and purified via column chromatography (silica-dry load, 2% MeOH in DCM (1% NH₄OH)) affording the title compound (1.1 g, 85%) as a white solid: LC-MS (ES) m/z=237 (M+H)⁺.

Preparation 2

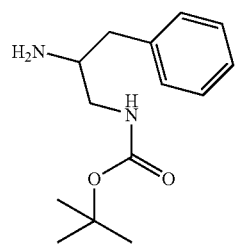

Preparation of 1,1-dimethylethyl(2-amino-3-phenylpropyl)carbamate a) 1-amino-3-phenyl-2-propanol

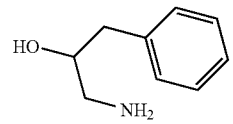

A solution of 2-(phenylmethyl)oxirane (7.5 g, 56.3 mmol) in NH₄OH (100 mL) was stirred at 25° C. in a sealed tube. After 12 h, the solution was concentrated and used directly: LCMS (ES) m/e 152 (M+H)⁺.

b) 1,1-dimethylethyl(2-hydroxy-3-phenylpropyl)carbamate

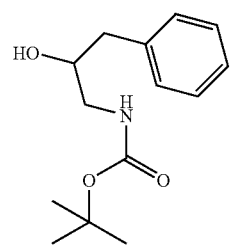

To a solution of 1-amino-3-phenyl-2-propanol (7.6 g, 50 mmole) in THF (50 mL) at RT was added (Boc)$_2$O (12.0 g, 55 mmole). After stirring at RT for 2 h, the reaction solution was concentrated under vacuum and the residue purified on silica gel (5% MeOH in DCM (0.5% NH$_4$OH)) affording the title compound (13.1 g, 91%) as a clear yellow oil: LCMS (ES) m/z 252 (M+H)$^+$.

c) 1,1-dimethylethyl[2-(1,3-dioxo-1,3-dihydro-2H-isoindol-2-yl)-3-phenylpropyl]carbamate

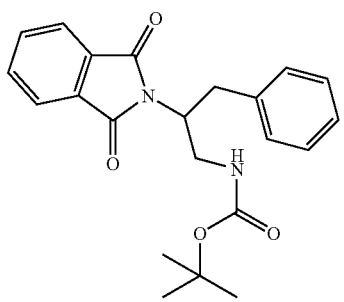

To a solution of 1,1-dimethylethyl(2-hydroxy-3-phenylpropyl)carbamate (10.0 g, 39.8 mmol), PPh$_3$ (12.5 g, 47.8 mmol) and phthalimide (6.44 g, 43.8 mmol) in THF (125 mL) at RT was added DEAD (9.4 mL, 59.7 mmol) over 5 min. After 1 h at RT, the reaction solution was concentrated and purified on silica (hexanes/EtOAc, 2:1) to give the title compound as a white solid (12.6 g, 83%): LCMS (ES) m/z 381 (M+H)$^+$.

c) 1,1-dimethylethyl(2-amino-3-phenylpropyl)carbamate

NH$_2$NH$_2$ (12.5 mL, 394 mmol) was added to a THF/MeOH (50 mL/50 mL) solution of 1,1-dimethylethyl(2-amino-4-phenylbutyl)carbamate (7.5 g, 19.7 mmol) and stirred at 50° C. in a sealed system. After 12 hours, the solids were filtered, washing with methanol. The filtrate was concentrated and purified by column chromatography using 5% MeOH in CHCl$_3$ containing 0.5% NH$_4$OH to give the title compound (3.75 g, 76%) as a white solid: LC-MS (ES) m/z=251 (M+H)$^+$.

Preparation 3

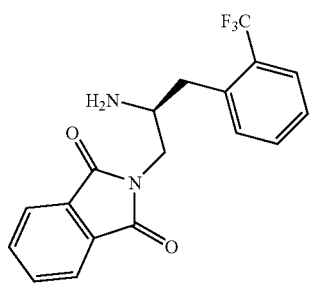

Preparation of 2-{(2S)-2-amino-3-[2-(trifluoromethyl)phenyl]propyl}-1H-isoindole-1,3(2H)-dione a) 1,1-dimethylethyl((1S)-2-hydroxy-1-{[2-(trifluoromethyl)phenyl]methyl}ethyl)carbamate

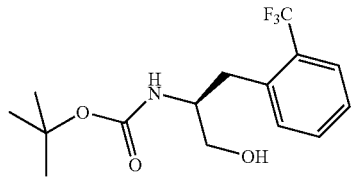

To a solution of N-{[(1,1-dimethylethypoxy]carbonyl}-2-(trifluoromethyl)-L-phenylalanine (5 g, 15 mmol) in THF (75 mL) at 0° C. stirred was added BH$_3$-THF (45 mL, 45 mmol-1M in THF). After 12 h, the reaction was quenched with AcOH:MeOH (1:5, 24 mL) and partitioned between saturated aqueous NaHCO$_3$ and DCM. The aqueous phase was then extracted several times with DCM. The combined organic fractions were dried over Na$_2$SO$_4$ and used directly (4.2 g, 88%): LCMS (ES) m/e 320 (M+H)$^+$.

b) 1,1-dimethylethyl((1S)-2-(1,3-dioxo-1,3-dihydro-2H-isoindol-2-yl)-1-{[2-(trifluoromethyl)phenyl]methyl}ethyl)carbamate

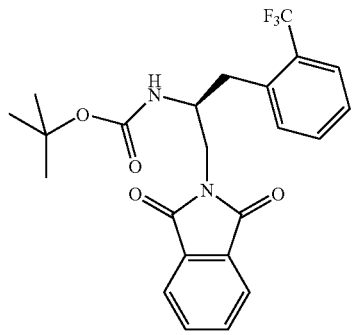

To a solution of 1,1-dimethylethyl((1S)-2-hydroxy-1-{[2-(trifluoromethyl)phenyl]methyl}ethyl)carbamate (4.2 g, 13.2 mmol), triphenylphosphine (4.5 g, 17.1 mmol) and phthalimide (1.9 g, 13.2 mmol) in THF (66 mL) at 25° C. was added diethyl azodicarboxylate (2.7 mL, 17.1 mmol). After stirring at RT for 1 h, the reaction solution was concentrated under vacuum and the residue purified on silica gel (1% MeOH in DCM) affording the title compound (3.2 g, 54%) as a white solid: LCMS (ES) m/z 449 (M+H)$^+$.

c) 1,1-dimethylethyl{(2S)-2-amino-3-[2(trifluoromethyl)phenyl]propyl}carbamate

To a solution of 1,1-dimethylethyl((1S)-2-(1,3-dioxo-1,3-dihydro-2H-isoindol-2-yl)-1-{[2-(trifluoromethyl)phenyl]methyl}ethyl)carbamate (3.2 g, 7.1 mmol) in MeOH (35 mL) at RT was added 4M HCl in dioxane (18 mL). After 12 h, the solution was concentrated affording the title compound (2.7 g, quant.) as the HCl salt: LCMS (ES) m/z 349 (M+H)⁺.

Preparation 4

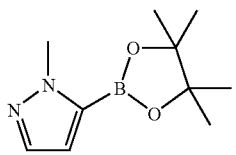

Preparation of 5-(5,5-dimethyl-1,3,2-dioxaborinan-2-yl)-1-methyl-1H-pyrazole

To a solution of 1-methyl pyrazole (4.1 g, 50 mmole) in THF (100 mL) at 0° C. was added n-BuLi (2.2M in THF, 55 mmole). The reaction solution was stirred for 1 hour at RT and then cooled to −78° C. [*J. Heterocyclic Chem.* 41, 931 (2004)]. To the reaction solution was added 2-isopropoxy-4,4,5,5-tetramethyl-1,3,2-dioxaborolane (12.3 mL, 60 mmole). After 15 min at −78° C., the reaction was allowed to warm to 0° C. over 1 hour. The reaction was diluted with saturated NH₄Cl solution and extracted with DCM. The organics were dried over Na₂SO₄ and concentrated under vacuum to afford a tan solid (8.0 g, 77%) which was used without further purification. LCMS (ES) m/z 127 (M+H)⁺ for [RB(OH)₂]; $^1$H NMR (CDCl₃, 400 MHz) δ 7.57 (s, 1H), 6.75 (s, 1H), 4.16 (s, 3H), and 1.41 (s, 12H).

Preparation 5

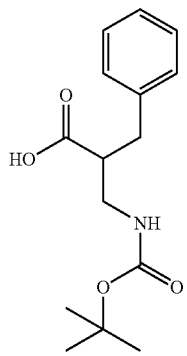

Preparation of 3-({[(1,1-dimethylethyl)oxy]carbonyl}amino)-2-(phenylmethyl)propanoic acid a) diethyl 2-[(1,3-dioxo-1,3-dihydro-2H-isoindol-2-yl)methyl]-2-(phenylmethyl)butanedioate

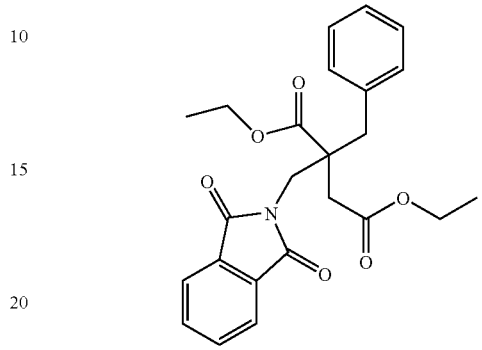

To a suspension of NaH (2.2 g, 54 mmole) in THF (200 mL) was added diethyl 2-(phenylmethyl)butanedioate (12.5 g, 49.9 mmole). After 30 min at RT, bromomethyl phthalimide was added to the reaction mixture and the contents were stirred for 14 h at RT. The reaction was quenched with H₂O (15 mL), diluted with Et₂O (300 mL) and layers separated. The organic layer was concentrated under vacuum and the resulting residue recrystallized from EtOH)(0°) to give the title compound (13 g, 64%) as a white solid: LCMS (ES) m/z 410 (M+H)⁺.

b) 3-amino-2-(phenylmethyl)propanoic acid

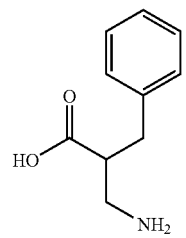

A solution of diethyl 2-[(1,3-dioxo-1,3-dihydro-2H-isoindol-2-yl)methyl]-2-(phenylmethyl)butanedioate (13 g, 31.8 mmole) in conc. HCl (125 mL) and HOAc (30 mL) was sealed in a 1 L screwcap reaction vessel and the contents heated to 120° C. for 48 h. The reaction solution was concentrated under vacuum and the resulting solids washed with Et₂O affording the title compound (quant.) as a white solid: LCMS (ES) m/z 181(M+H)⁺.

c) 3-({[(1,1-dimethylethyl)oxy]carbonyl}amino)-2-(phenylmethyl)propanoic acid

To a solution of 3-amino-2-(phenylmethyl)propanoic acid (from previous reaction) in dioxane (100 mL) and H₂O (20 mL) was added Boc anhydride (10.1 g, 46.5 mmole) and 6M NaOH solution (26 mL). After stirring at RT for 12 h, the reaction solution was concentrated under vacuum, neutralized with 3M HCl and extracted with DCM. The organic layer was dried over Na₂SO₄ and concentrated to a viscous oil. The oil was washed with pentane and dried under high vacuum to give the title compound (5.0 g, 17.9 mmole, 58% for 2 steps) as a white solid: LCMS (ES) m/z 280 (M+H)⁺.

Preparation 6

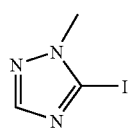

Preparation of 5-iodo-1-methyl-1H-1,2,4-triazole 1-methyl-1H-1,2,4-triazole (2.05 g, 24.7 mmol) was added slowly over 15 minutes to an Et$_2$O solution of nBuLi at −70° C. The mixture was stirred for 60 minutes at −70° C. and allowed to warm to −30° C. A solution of I$_2$ (6.5 g, 25.6 mmol) in THF (27 mL) was added slowly over 15 minutes and the mixture was allowed to warm to room temperature and stir for 60 minutes. The mixture was partitioned with saturated Na$_2$S$_2$O$_3$, the phases were separated and the organic solvent removed. The crude iodide was used without further purification: LCMS (ES) m/z 210 (M+H)⁺.

Example 1

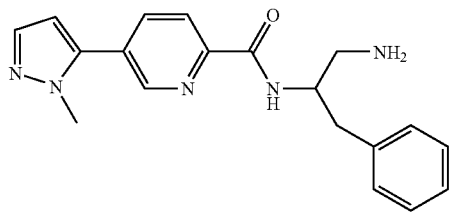

Preparation of N-[2-amino-1-(phenylmethyl)ethyl]-5-(1-methyl-1H-pyrazol-5-yl)-2-pyridinecarboxamide a) 1,1-dimethylethyl(2-{[(5-bromo-2-pyridinyl)carbonyl]amino}-3-phenylpropyl)carbamate

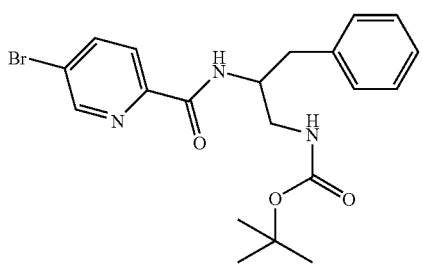

To a solution of 5-bromo-2-pyridinecarboxylic acid (0.52 g, 2.6 mmol), PyBrOP (1.4 g, 3.0 mmol) and diisopropylethyl amine (1.0 mL, 6.0 mmol) in DCM (70 mL) at 25° C. was added 1,1-dimethylethyl(2-amino-3-phenylpropyl)carbamate (0.5 g, 2.0 mmol). After 16 h, the solution was partitioned between H$_2$O and washed with DCM. The combined organic fraction were dried (Na$_2$SO$_4$), concentrated and purified via column chromatography (silica, hexanes/EtOAc, 1:1) affording the title compound (0.60 g, 69%) as a white solid: LC-MS (ES) m/z=435 (M+H)⁺.

b) 1,1-dimethylethyl[2-({[5-(1-methyl-1H-pyrazol-5-yl)-2-pyridinyl]carbonyl}amino)-3-phenylpropyl]carbamate

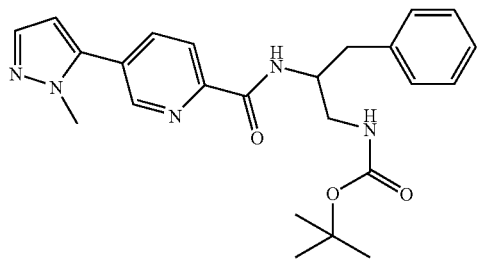

To a solution of 1,1-dimethylethyl(2-{[(5-bromo-2-pyridinyl)carbonyl]amino}-3-phenylpropyl)carbamate (0.58 g, 1.34 mmol) in dioxane/H$_2$O (5:1, 55 mL) was added K$_2$CO$_3$ (0.55 g, 4.0 mmol), tetrakistriphenylphosphine Pd(0) (0.15 mg, 0.13 mmol), and 5-(5,5-dimethyl-1,3,2-dioxaborinan-2-yl)-1-methyl-1H-pyrazole (0.39 g, 2.0 mmol). The reaction mixture was heated to 80° C. in a sealed tube for 12 h. The reaction solution was poured onto H$_2$O (100 mL) and extracted with DCM. The organics were dried (Na$_2$SO$_4$), concentrated under vacuum, and purified on silica gel (DCM/MeOH, 95:5) to give the title compound (0.39 g, 67%) as a white solid: LC-MS (ES) m/z=436 (M+H)⁺.

c) N-[2-amino-1-(phenylmethyl)ethyl]-5-(1-methyl-1H-pyrazol-5-yl)-2-pyridinecarboxamide 1,1-dimethylethyl[2-({[5-(1-methyl-1H-pyrazol-5-yl)-2-pyridinyl]carbonyl}amino)-3-phenylpropyl]carbamate (0.39 g, 0.90 mmol) was dissolved in MeOH (10 mL) and THF (5 mL) and treated with 4M HCl in dioxane (5 mL). After 3 h, the solution was concentrated affording the HCl salt of the title compound (0.32 g, 90%) as a white powder: LC-MS (ES) m/z=336 (M+H)⁺)⁺, ¹H NMR (d$_4$-MeOH, 400 MHz) δ 8.87 (s, 1H), 8.22 (m, 2H), 7.81 (s, 1H), 7.32 (m, 4H), 7.24 (m, 1H), 6.73 (s, 1H), 4.62 (m, 1H), 4.00 (s, 1H), 3.27 (m, 2H), 3.05 (d, J=7.3 Hz, 2H).

Example 2

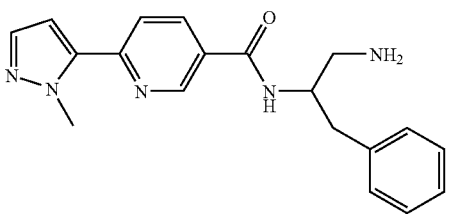

Preparation of N-[2-amino-1-(phenylmethyl)ethyl]-6-(1-methyl-1H-pyrazol-5-yl)-3-pyridinecarboxamide The title compound was prepared as a white solid according to the example of Example 1, except substituting 2-bromo-5-pyridinecarboxylic acid (0.52 g, 2.6 mmol) for 5-bromo-2-pyridinecarboxylic acid: LC-MS (ES) m/z 336 (M+H)$^+$, $^1$H NMR (d$_4$-MeOH, 400 MHz) δ 9.10 (s, 1H), 8.43 (d, J=8.3 Hz, 1H), 8.04 (d, J=8.3 Hz, 1H), 7.82 (d, J=2.3 Hz, 1H), 7.35 (m, 4H), 7.30 (m, 1H), 7.01 (s, 1H), 4.59 (m, 1H), 4.39 (s, 3H), 3.26 (m, 2H), 3.05 (m, 2H).

Example 3

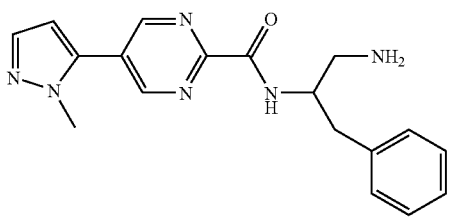

Preparation of N-(2-amino-1-benzylethyl)-5-(1-methyl-1H-pyrazol-5-yl)pyrimidine-2-carboxamide a) 5-(1-methyl-1H-pyrazol-5-yl)pyrimidine-2-carboxylic acid

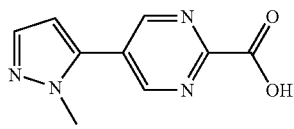

To a solution of 1-methyl-5-(4,4,5,5-tetramethyl-1,3,2-dioxaborolan-2-yl)-1H-pyrazole (1.35 g, 6.5 mmol) in dioxane/H$_2$O (5:1, 59 mL) was added K$_2$CO$_3$ (2.8 g, 20.3 mmol), tetrakistriphenylphosphine Pd(0) (340 mg, 0.3 mmol), and 5-bromo-2-pyrimidinecarboxylic acid (1.2 g, 5.9 mmol). The reaction mixture was heated to 80° C. in a sealed tube for 12 h. The reaction solution was poured onto H$_2$O (100 mL) and extracted with DCM. The organics were dried (Na$_2$SO$_4$), concentrated under vacuum to give the title compound (0.9 g, 36%) as a tan solid: LC-MS (ES) m/z=437 (M+H)$^+$.

b) 1,1-dimethylethyl[2-({[5-(1-methyl-1H-pyrazol-5-yl)-2-pyrimidinyl]carbonyl}amino)-3-phenylpropyl]carbamate

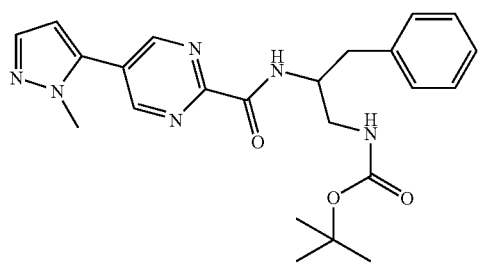

To a solution of 5-(1-methyl-1H-pyrazol-5-yl)pyrimidine-2-carboxylic acid (194 mg, 0.4 mmol), PyBrOP (330 mg, 0.71 mmol) and diisopropylethyl amine (0.27 mL, 1.5 mmol) in DCM (7 mL) at 25° C. was added 1,1-dimethylethyl(2-amino-3-phenylpropyl)carbamate (174 mg, 0.7 mmol). After 16 h, the solution was concentrated and purified via column chromatography (silica, hexanes/EtOAc, 2:1) affording the title compound (76 mg, 39%) as a white solid: LC-MS (ES) m/z=437 (M+H)$^+$.

c) N-(2-amino-1-benzylethyl)-5-(1-methyl-1H-pyrazol-5-yl)pyrimidine-2-carboxamide 1,1-dimethylethyl[2-({[5-(1-methyl-1H-pyrazol-5-yl)-2-pyrimidinyl]carbonyl}amino)-3-phenylpropyl]carbamate (76 mg, 0.17 mmol) was dissolved in MeOH (1 mL) and CHCl$_3$ (10 mL) and treated with 4M HCl in dioxane (5 mL). After 3 h, the solution was concentrated and purified via column chromatography (silica, CHCl$_3$/MeOH, 90:10 containing 1% NH$_4$OH affording the free base of the title compound (40 mg, 68%) as a white powder.

The HCl salt was made by addition of an excess of 1M HCl in Et$_2$O to yield the final compound as the HCl salt: LC-MS (ES) m/z=337 (M+H)$^+$, $^1$H NMR (d$_4$-MeOH, 400 MHz) δ ppm 2.91-3.01 (m, 4H) 4.00 (s, 3H) 4.37-4.46 (m, 1H) 6.69 (d, J=2.02 Hz, 1H) 7.18 (t, J=7.20 Hz, 1H) 7.23-7.33 (m, 4H) 7.62 (d, J=2.02 Hz, 1 H) 9.11 (s, 2H).

Example 4

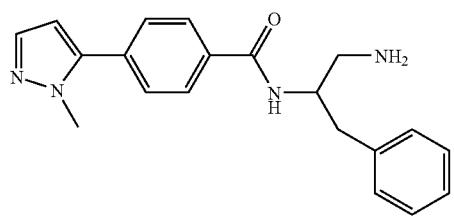

Preparation of N-[2-amino-1-(phenylmethyl)ethyl]-4-(1-methyl-1H-pyrazol-5-yl)benzamide The title compound was prepared as a white solid according to the procedure of Example 3, except substituting 4-bromobenzoic acid (102 mg, 0.5 mmol) for 5-bromo-2-pyrimidinecarboxylic acid: LC-MS (ES) m/z=335 (M+H)$^+$, $^1$H NMR (d$_4$-MeOH, 400 MHz) δ 7.96 (d, J=12 Hz, 2H), 7.63 (d, J=12 Hz, 2H), 7.4 (m, 1H), 7.34 (m, 4H), 7.23 (m, 1H), 6.58 (s, 1H), 4.63 (m, 1H), 3.96 (s, 3H), 3.25 (m, 2H), 3.05 (m, 2H).

Example 5

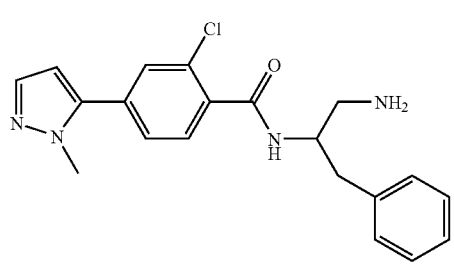

Preparation of N-[2-amino-1-(phenylmethyl)ethyl]-2-chloro-4-(1-methyl-1H-pyrazol-5-yl)benzamide The title compound was prepared as a white solid according to the procedure of Example 3, except substituting 4-bromo-2-chlorobenzoic acid (118 mg, 0.5 mmol) for 5-bromo-2-pyrimidinecarboxylic acid: LC-MS (ES) m/z=369 (M+H)+, 1H NMR (d4-MeOH, 400 MHz) δ 7.70 (s, 1H), 7.65 (m, 1H), 7.54 (m, 2H), 7.36 (m, 4H), 7.29 (m, 1H), 6.57 (m, 1H), 4.63 (m, 1H), 4.89 (s, 3H), 3.21 (m, 2H), 3.08 (m, 1H), 2.98 (m, 1H).

Example 6

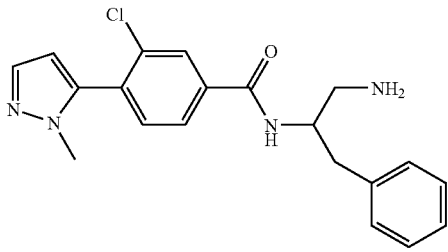

Preparation of N-[2-amino-1-(phenylmethyl)ethyl]-3-chloro-4-(1-methyl-1H-pyrazol-5-yl)benzamide The title compound was prepared as a yellow solid according to the procedure of Example 3, except substituting 4-bromo-3-chlorobenzoic acid (118 mg, 0.5 mmol) for 5-bromo-2-pyrimidinecarboxylic acid: LC-MS (ES) m/z=369 (M+H+)+, 1H NMR (d4-MeOH, 400 MHz) δ 8.03 (s, 1H), 7.9 (m, 2H), 7.6 (m, 1H), 7.38 (m, 1H), 7.32 (m, 1H), 7.25 (m, 1H), 6.64 (m, 1H), 4.62 (m, 1H), 3.83 (s, 3H), 3.24 (m, 2H), 3.04 (m, 2H).

Example 7

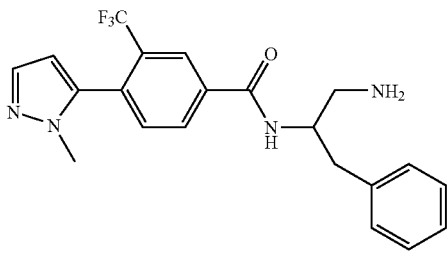

Preparation of N-[2-amino-1-(phenylmethyl)ethyl]-4-(1-methyl-1H-pyrazol-5-yl)-3-(trifluoromethyl)benzamide a) 1,1-dimethylethyl[2-({[4-hydroxy-3-(trifluoromethyl)phenyl]carbonyl}amino)-3-phenylpropyl]carbamate

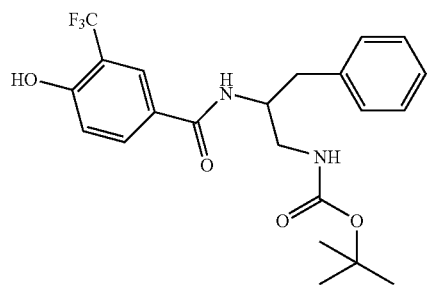

To a solution of 4-hydroxy-3-trifluoromethylbenzoic acid (0.54 mg, 2.6 mmol), PyBrOP (0.77 g, 6.0 mmol) and diisopropylethyl amine (1 mL, 6.0 mmol) in DCM (50 mL) at 25° C. was added 1,1-dimethylethyl(2-amino-3-phenylpropyl)carbamate (0.50 mg, 2.0 mmol). After 12 h, the solution was concentrated and purified on silica (EtOAc/hexanes, 2:1) to give the title compound (0.19 g, 17%) as a colorless oil: LC-MS (ES) m/z=439 (M+H)+.

b) 4-({[2-({[(1,1-dimethylethyl)oxy]carbonyl}amino)-1-(phenylmethyl)ethyl]amino}carbonyl)-2-(trifluoromethyl)phenyl trifluoromethanesulfonate

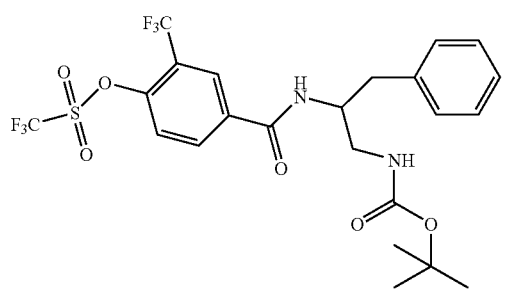

To a solution of 1,1-dimethylethyl[2-({[4-hydroxy-3-(trifluoromethyl)phenyl]carbonyl}amino)-3-phenylpropyl]carbamate (0.18 g, 0.41 mmoles) in DCM (15 mL) at room temperature was added triethylamine (0.17 mL, 1.2 mmol) and N-phenyltrifluoromethane sulfonimide (0.19 g, 0.53 mmoles). After 24 h, the solution was concentrated and purified via column chromatography (silica, hexanes/EtOAc, 4:1) yielding the the tilte compound (100 mg, 43%) as a white solid: LC-MS (ES) m/z=571 (M+H)+.

c) 1,1-dimethylethyl[2-({[4-(1-methyl-1H-pyrazol-5-yl)-3-(trifluoromethyl)phenyl]carbonyl}amino)-3-phenylpropyl]carbamate

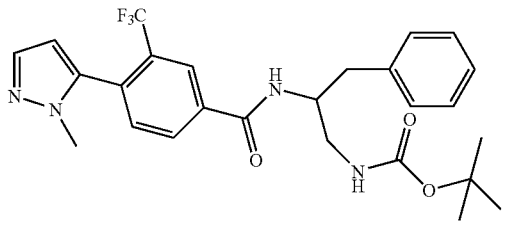

To a solution of 4-({[2-({[(1,1-dimethylethyl)oxy]carbonyl}amino)-1-(phenylmethyl)ethyl]amino}carbonyl)-2-(trifluoromethyl)phenyl trifluoromethanesulfonate (0.21 g, 0.37 mmol) in dioxane/H$_2$O (5:1, 10 mL) was added K$_2$CO$_3$ (150 mg, 1.1 mmol), tetrakistriphenylphosphine Pd(0) (46 mg, 37 umol) and 5-(5,5-dimethyl-1,3,2-dioxaborinan-2-yl)-1-methyl-1H-pyrazole (140 mg, 0.74 mmol). The reaction mixture was heated to 80° C. in a sealed tube for 12 h. The reaction solution was poured onto H$_2$O (100 mL) and extracted with DCM. The organics were dried (Na$_2$SO$_4$), concentrated under vacuum and purified on silica (EtOAc) to give the title compound (0.16 g, 86%) as a white solid: LC-MS (ES) m/z=503 (M+H)$^+$.

d) N-[2-amino-1-(phenylmethyl)ethyl]-4-(1-methyl-1H-pyrazol-5-yl)-3-(trifluoromethyl)benzamide 1,1-dimethylethyl[2-({[4-(1-methyl-1H-pyrazol-5-yl)-3-(trifluoromethyl)phenyl]carbonyl}amino)-3-phenylpropyl]carbamate (0.16 g, 0.32 mmoles) was dissolved in MeOH (10 mL) and THF (3 mL) and treated with excess 4M HCl in dioxane. After 2 h at RT, the reaction solution was concentrated under vacuum affording the HCl salt of the title compound (150 mg, quant.) as a white solid: LC-MS (ES) m/z=403 (M+H)$^+$, $^1$H NMR (MeOD, 400 MHz) δ 8.29 (s, 1H), 8.17 (d, J=7.8 Hz, 1H), 7.84 (s, 1H), 7.34 (m, 4H), 7.25 (m, 1H), 6.53 (s, 1H), 4.65 (m, 1H), 3.73 (s, 3H), 3.26 (m, 2H) and 3.04 (m, 2H).

Example 8

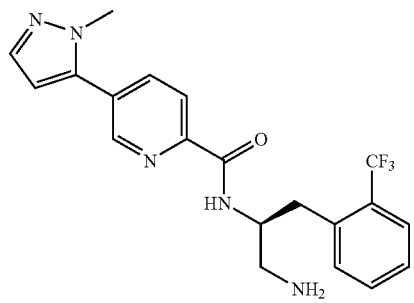

Preparation of N-((1S)-2-amino-1-{[2-(trifluoromethyl)phenyl]methyl}ethyl)-5-(1-methyl-1H-pyrazol-5-yl)-2-pyridinecarboxamide a) 5-bromo-N-((1S)-2-(1,3-dioxo-1,3-dihydro-2H-isoindol-2-yl)-1-{[2-(trifluoromethyl)phenyl]methyl}ethyl)-2-pyridinecarboxamide

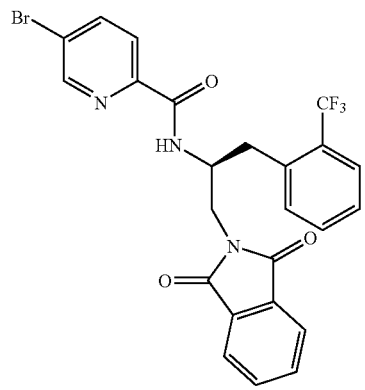

To a solution of 5-bromo-2-pyridinecarboxylic acid (97 mg, 2.6 mmol), PyBrOP (269 mg, 0.578 mmol) and diisopropylethylamine (419 uL, 2.41 mmol) in DCM (5 mL) at 25° C. was added 2-{(2S)-2-amino-3-[2-(trifluoromethyl)phenyl]propyl}-1H-isoindole-1,3(2H)-dione (168 mg, 0.481 mmol) [prepared in preparation 3]. After 16 h, the solution was partitioned between H$_2$O and washed with DCM. The combined organic fraction were dried (Na$_2$SO$_4$), concentrated and used directly without further purification: LC-MS (ES) m/z=435 (M+H)$^+$.

b) 1,1-dimethylethyl{(2S)-2-{[(5-bromo-2-pyridinyl)carbonyl]amino}-3-[2-(trifluoromethyl)phenyl]propyl}carbamate

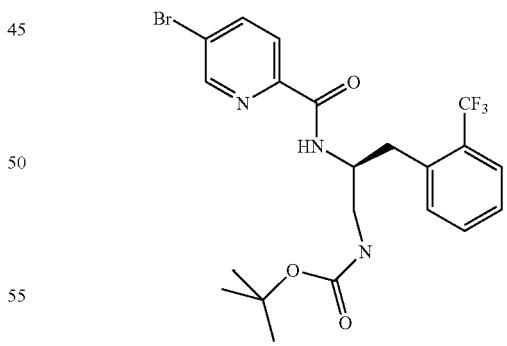

i) To a solution of 5-bromo-N-((1S)-2-(1,3-dioxo-1,3-dihydro-2H-isoindol-2-yl)-1-{[2-(trifluoromethyl)phenyl]methyl}ethyl)-2-pyridinecarboxamide (crude from part a) in MeOH-THF (1:1, 5 mL) was added hydrazine (151 uL, 4.80 mmol) at 25° C. After 12 h, the solution was filtered and the filtrate was concentrated. The resulting residue was purified via column chromatography (silica, 2% MeOH in DCM (1% NH$_4$OH)) affording the free base (192 mg, quant.) of the title compound: LCMS (ES) m/e 402 (M+H)$^+$.

ii) The free base (192 mg, 0.478 mmol) was dissolved in THF (6 mL) and treated with Boc₂O (144 mg, 0.669 mmol). After 30 min, the solution was concentrated affording the title compound (300 mg, quant.) as a clear oil which was used directly: LCMS (ES) m/e 502 (M+H)⁺.

c) 1,1-dimethylethyl{(2S)-2-({[5-(1-methyl-1H-pyrazol-5-yl)-2-pyridinyl]carbonyl}amino)-3-[2-(trifluoromethyl)phenyl]propyl}carbamate

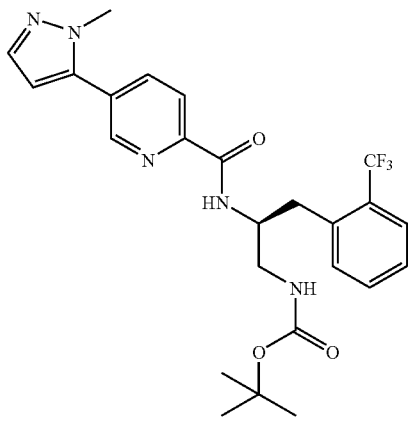

To a solution of 1,1-dimethylethyl{(2S)-2-{[(5-bromo-2-pyridinyl)carbonyl]amino}-3-[2-(trifluoromethyl)phenyl]propyl}carbamate (300 mg, 0.60 mmol) in dioxane/H₂O (5:1, 6 mL) was added K₂CO₃ (331 mg, 2.4 mmol), tetrakistriphenylphosphine Pd(0) (35 mg, 29.9 mmol), and 5-(5,5-dimethyl-1,3,2-dioxaborinan-2-yl)-1-methyl-1H-pyrazole (162 mg, 0.78 mmol). The reaction mixture was heated to 80° C. in a sealed tube for 12 h. The reaction solution was poured onto H₂O (100 mL) and extracted with DCM. The organics were dried (Na₂SO₄) and concentrated under vacuum affording the title compound which was used directly without further purification: LC-MS (ES) m/z=504 (M+H)⁺.

d) N-((1S)-2-amino-1-{[2-(trifluoromethyl)phenyl]methyl}ethyl)-5-(1-methyl-1H-pyrazol-5-yl)-2-pyridinecarboxamide 1,1-dimethylethyl{(2S)-2-({[5-(1-methyl-1H-pyrazol-5-yl)-2-pyridinyl]carbonyl}amino)-3-[2-(trifluoromethyl)phenyl]propyl}carbamate (crude from part c) was dissolved in DCM (2 mL) and treated with TFA (1 mL). After 30 min., the solution was concentrated and neutralized through a plug of silica (2% MeOH in DCM (1% NH4OH)) affording the free base of the title compound.

The free base was dissolved in MeOH (2 mL) and treated with excess 4M HCl in dioxane (500 uL) affording the HCl salt of the title compound (110 mg, 45%-3 steps) as a white solid: LCMS (ES) m/z=404 (M+H)⁺, ¹H NMR (400 MHz, DMSO-d₆) δ ppm 9.07 (d, J=9.60 Hz, 1H) 8.85 (d, J=1.52 Hz, 1H) 8.18 (dd, J=8.08, 2.27 Hz, 1H) 8.03 (d, J=8.08 Hz, 4H) 7.69 (d, J=7.83 Hz, 1H) 7.57 (d, J=2.02 Hz, 1H) 7.47-7.54 (m, 2H) 7.41 (dd, J=7.96, 2.15 Hz, 1H) 6.65 (d, J=2.02 Hz, 1H) 4.51-4.55 (m, 1H) 3.92 (s, 3H) 3.13-3.16 (m, 4H).

Example 9

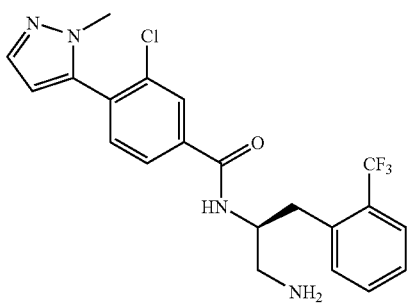

Preparation of N-((1S)-2-amino-1-{[2-(trifluoromethyl)phenyl]methyl}ethyl)-3-chloro-4-(1-methyl-1H-pyrazol-5-yl)benzamide The title compound was prepared as a white solid according to the procedure of Example 8, except substituting 4-bromo-3-chlorobenzoic acid (88 mg, 0.372 mmol) for 5-bromo-2-pyridinecarboxylic acid: LCMS (ES) m/z=437 (M+H)⁺, ¹H NMR (400 MHz, DMSO-d₆) δ ppm 8.88 (br. s., 1H) 8.08 (bs, 4H) 7.87 (br. s., 1 H) 7.71 (d, J=7.83 Hz, 1H) 7.54-7.61 (m, 4H) 7.44 (s, 1H) 6.40 (d, J=1.77 Hz, 1 H) 4.59 (d, J=4.80 Hz, 1H) 3.66 (s, 3H) 3.06-3.17 (m, 4H).

Example 10

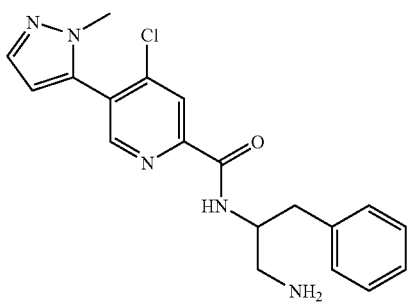

Preparation of N-[2-amino-1-(phenylmethyl)ethyl]-4-chloro-5-(1-methyl-1H-pyrazol-5-yl)-2-pyridinecarboxamide a) 5-bromo-2-methylpyridine N-oxide

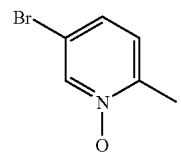

To a solution of 5-bromo-2-methylpyridine (1 g, 5.81 mmol) and urea hydrogen peroxide (1.1 g, 12.2 mmol) in DCM (30 mL) at 0° C. was added trifluoroacetic anhydride (1.6 mL, 11.6 mmol). After warming to 25° C. over 12 h, the solution was partitioned between H₂O-DCM. The aqueous phase was washed several times with DCM and the combined organic fractions were dried over Na₂SO₄, concentrated and purified via column chromatography (silica, 1% MeOH in DCM (1% NH₄OH)) yielding the title compound (660 mg, 60%) as a white solid: LCMS (ES) m/z=190 (M+H)⁺.

b) 5-bromo-2-methyl-4-nitropyridine N-oxide

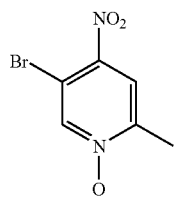

To a solution of 5-bromo-2-methylpyridine N-oxide (660 mg, 3.51 mmol) in sulfuric acid (1.6 mL) at 0° C. was added a premixed solution of nitric acid (1.5 mL) in sulfuric acid (2.5 mL). The resulting reaction was warmed to 25° C. then heated to 80° C. After 12 h, the solution was poured into ice then, neutralized with 6N NaOH and extracted several times with DCM. The combined organic fractions were dried over Na₂SO₄, concentrated and purified via column chromatography (silica, 1% MeOH in DCM) yielding the title compound (558 mg, 81%) as a yellow solid: LCMS (ES) m/z=235 (M+H)⁺.

c) 5-bromo-4-chloro-2-methylpyridine N-oxide

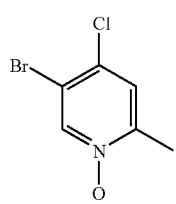

To a solution of 5-bromo-2-methyl-4-nitropyridine N-oxide (558 mg, 2.41 mmol) in DCM (3 mL) at 0° C. was added dropwise a solution of POCl₃ (1.3 mL, 7.22 mmol) in DCM (3.2 mL). After 12 h at 25° C. the solution was added to ice, adjusted to pH ~8 and extracted several times with DCM. The combined organic fractions were dried over Na₂SO₄, concentrated and purified via column chromatography (silica, 1.5% MeOH in DCM) yielding the title compound (426 mg, 80%) as a white solid: LCMS (ES) m/z=224 (M+H)⁺.

d) 5-bromo-4-chloro-2-pyridinyl)methanol

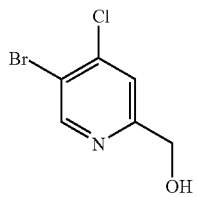

To a solution of 5-bromo-2-methyl-4-nitropyridine N-oxide (426 mg, 1.93 mmol) in DCM (5 mL) at 0° C. was added trifluoroacetic anhydride (817 uL, 5.78 mmol). After warming to 25° C. over 12 h, the solution was partitioned between 6N NaOH-DCM. The aqueous phase was washed several times with DCM and the combined organic fractions were dried over Na₂SO₄, concentrated and purified via column chromatography (silica, 1% MeOH in DCM) yielding the title compound (187 mg, 44%) as a white solid: LCMS (ES) m/z=223 (M+H)⁺.

e) 5-bromo-4-chloro-2-pyridinecarboxylic acid

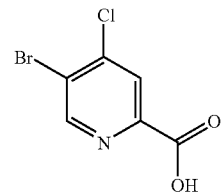

KMnO₄ (174 mg, 1.1 mmol) in H₂O was added dropwise to a solution of (5-bromo-4-chloro-2-pyridinyl)methanol (187 mg, 0.846 mmol) in 10% Na₂CO₃ (1 mL). After 2 h, the solution was filtered through Celite®, adjusted to pH ~4 and the resulting precipitate was filtered then azeotropically dried with toluene affording the title compound (135 mg, 68%) as a white powder: LCMS (ES) m/z=237 (M+H)⁺.

f) N-[2-amino-1-(phenylmethyl)ethyl]-4-chloro-5-(1-methyl-1H-pyrazol-5-yl)-2-pyridinecarboxamide The title compound was prepared as a white solid according to the example of Example 1, except substituting 5-bromo-4-chloro-2-pyridinecarboxylic acid (135 mg, 0.572 mmol) for 5-bromo-2-pyridinecarboxylic acid: LCMS (ES) m/z=370 (M+H)⁺, ¹H NMR (400 MHz, DMSO-d₆) δ ppm 9.07 (d, J=9.35 Hz, 1H) 8.75 (s, 1H) 8.14 (s, 1H) 8.03 (br. s., 3H) 7.61 (d, J=2.02 Hz, 1H) 7.26 (d, J=3.28 Hz, 3H) 7.23-7.30 (m, 1H) 7.17-7.22 (m, 1H) 6.53 (d, J=2.02 Hz, 1H) 4.53 (d, J=4.29 Hz, 1H) 3.71 (s, 3H) 2.96-3.17 (m, 4H).

Example 11

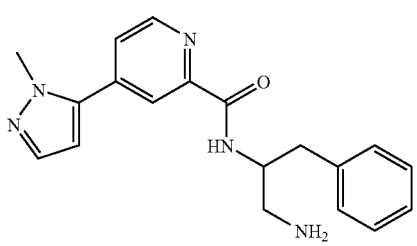

Preparation of N-[2-amino-1-(phenylmethyl)ethyl]-4-(1-methyl-1H-pyrazol-5-yl)-2-pyridinecarboxamide The title compound was prepared as a white solid according to the procedure of Example 1, except substituting 4-bromo-2-pyridinecarboxylic acid (300 mg, 1.48 mmol) for 5-bromo-2-pyridinecarboxylic acid: LCMS (ES) m/z=436 (M+H)+, 1H NMR (400 MHz, DMSO-d6) δ ppm 8.99 (d, J=9.09 Hz, 1H) 8.77 (d, J=5.05 Hz, 1H) 8.08 (d, J=1.01 Hz, 1H) 8.01 (s, 3H) 7.84 (dd, J=5.05, 1.77 Hz, 1 H) 7.57 (d, J=2.02 Hz, 1H) 7.23-7.30 (m, 4H) 7.19 (td, J=6.19, 2.53 Hz, 1H) 6.71 (d, J=1.77 Hz, 1H) 4.52 (m, 1H) 3.96 (s, 3H) 2.97-3.10 (m, 4H).

Example 12

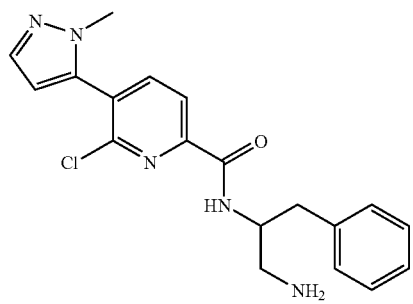

Preparation of N-[2-amino-1-(phenylmethyl)ethyl]-6-chloro-5-(1-methyl-1H-pyrazol-5-yl-2-pyridinecarboxamide a) 3-bromo-2-chloro-6-methylpyridine N-oxide

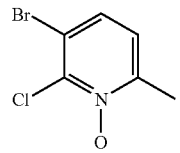

To a solution of 3-bromo-2-chloro-6-methylpyridine (1 g, 4.84 mmol) and urea hydrogen peroxide (911 mg, 9.69 mmol) in DCM (24 mL) at 0° C. was added trifluoroacetic anhydride (1.4 mL, 9.69 mmol). After warming to 25° C. over 12 h, the solution was partitioned between H2O-DCM. The aqueous phase was washed several times with DCM and the combined organic fractions were dried over Na2SO4, concentrated and purified via column chromatography (silica, 1% MeOH in DCM) yielding the title compound (1.1 g, quant.) as a white solid: LCMS (ES) m/z=223 (M+H)+.

b) N-[2-amino-1-(phenylmethyl)ethyl]-6-chloro-5-(1-methyl-1H-pyrazol-5-yl)-2-pyridinecarboxamide The title compound was prepared as a white solid according to Example 10, except substituting 3-bromo-2-chloro-6-methylpyridine N-oxide (1.1 g, 4.95 mmol) for 5-bromo-4-chloro-2-methylpyridine N-oxide: LCMS (ES) m/z=370 (M+H)+, 1H NMR (400 MHz, DMSO-d6) δ ppm 8.83 (d, J=9.35 Hz, 1H) 8.10-8.17 (m, 1H) 8.06 (d, J=7.83 Hz, 4H) 7.58 (d, J=2.02 Hz, 1H) 7.24-7.32 (m, 4H) 7.18-7.23 (m, 1 H) 6.49 (d, J=1.77 Hz, 1H) 4.53 (d, J=3.79 Hz, 1H) 3.70 (s, 3H) 3.17 (s, 1H) 2.98 (d, J=7.83 Hz, 3H).

Example 13

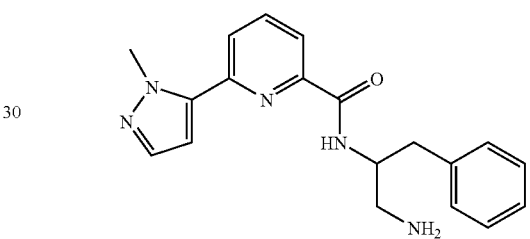

Preparation of N-[2-amino-1-(phenylmethyl)ethyl]-6-(1-methyl-1H-pyrazol-5-yl)-2-pyridinecarboxamide The title compound was prepared as a white solid according to the procedure of Example 3, except substituting 6-bromo-2-pyridinecarboxylic acid (1.2 g, 5.9 mmol) for 5-bromo-2-pyrimidinecarboxylic acid: LC-MS (ES) m/z 336 (M+H)+, 1H NMR (400 MHz, MeOD) δ ppm 2.98-3.09 (m, 4H) 4.07 (s, 3H) 4.51 (ddd, J=7.89, 4.99, 2.53 Hz, 1H) 6.77 (d, J=2.02 Hz, 1H) 7.17-7.22 (m, 1H) 7.23-7.30 (m, 4H) 7.54 (d, J=2.27 Hz, 1H) 7.89 (q, J=4.55 Hz, 1H) 8.04 (d, J=4.04 Hz, 2H).

Example 14

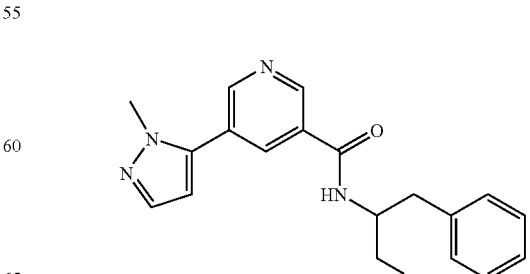

Preparation of N-[2-amino-1-(phenylmethyl)ethyl]-5-(1-methyl-1H-pyrazol-5-yl)-3-pyridinecarboxamide The title compound was prepared as a white solid according to the procedure of Example 3, except substituting 5-bromo-3-pyridinecarboxylic acid (2.1 g, 10.4 mmol) for 5-bromo-2-pyrimidinecarboxylic acid: LC-MS (ES) m/z 336 (M+H)+, 1H NMR (400 MHz, MeOD) δ ppm 2.77-3.04 (m, 4H) 3.91 (s, 3H) 4.39 (s, 1H) 6.54 (d, J=2.02 Hz, 1H) 7.16-7.23 (m, 1H) 7.25-7.31 (m, 4H) 7.58 (d, J=2.02 Hz, 1H) 8.23 (t, J=2.15 Hz, 1H) 8.81 (d, J=2.27 Hz, 1H) 8.92 (d, J=2.02 Hz, 1H).

Example 15

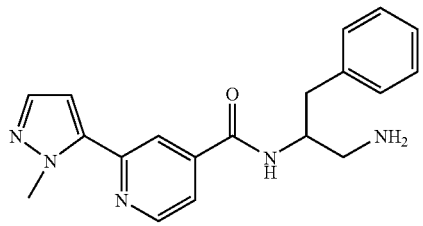

Preparation N-[2-amino-1-(phenylmethyl)ethyl]-2-(1-methyl-1H-pyrazol-5-yl)-4-pyridinecarboxamide The title compound was prepared as a white solid according to the procedure of Example 3, except substituting 2-bromo-4-pyridinecarboxylic acid (1.0 g, 5.2 mmol) for 5-bromo-2-pyrimidinecarboxylic acid: LC-MS (ES) m/z 336 (M+H)+, 1H NMR (400 MHz, MeOD) δ ppm 2.84-2.94 (m, 2H) 2.96-3.02 (m, 2H) 4.16 (s, 3H) 4.40 (ddd, J=8.34, 4.80, 2.27 Hz, 1H) 6.75 (d, J=2.02 Hz, 1H) 7.19 (td, J=6.00, 2.65 Hz, 1H) 7.25-7.30 (m, 4H) 7.53 (d, J=2.02 Hz, 1H) 7.60 (dd, J=5.18, 1.64 Hz, 1H) 7.95 (s, 1H) 8.73 (d, J=5.31 Hz, 1H).

Example 16

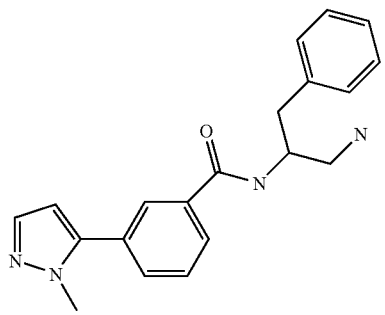

Preparation of N-[2-amino-1-(phenylmethyl)ethyl]-3-(1-methyl-1H-pyrazol-5-yl)benzamide The title compound was prepared as a white solid according to the procedure of Example 3, except substituting 3-bromo-benzoic acid (101 mg, 0.5 mmol) for 5-bromo-2-pyrimidinecarboxylic acid: LC-MS (ES) m/z 335 (M+H)+, 1H NMR (400 MHz, MeOD) δ ppm 3.01-3.08 (m, 2H) 3.21-3.28 (m, 2H) 4.00 (d, J=1.77 Hz, 3H) 4.60-4.67 (m, 1H) 6.71 (d, J=2.53 Hz, 1H) 7.20-7.25 (m, 1H) 7.29-7.35 (m, 4H) 7.66 (t, J=7.71 Hz, 1H) 7.76 (dd, J=7.83, 1.26 Hz, 1H) 7.92-7.97 (m, 3H).

Example 17

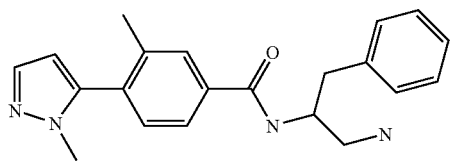

Preparation of N-[2-amino-1-(phenylmethyl)ethyl]-3-methyl-4-(1-methyl-1H-pyrazol-5-yl)benzamide The title compound was prepared as a white solid according to the procedure of Example 3, except substituting 4-bromo-3-methylbenzoic acid (108 mg, 0.5 mmol) for 5-bromo-2-pyrimidinecarboxylic acid: LC-MS (ES) m/z 349 (M+H)+, 1H NMR (400 MHz, MeOD) δ ppm 2.28 (s, 3H) 3.02-3.08 (m, 2H) 3.21-3.28 (m, 2H) 3.80 (s, 3H) 4.59-4.67 (m, 1H) 6.62-6.63 (m, 1H) 7.22-7.27 (m, 1H) 7.30-7.36 (m, 4H) 7.43 (d, J=8.08 Hz, 1H) 7.76 (dd, J=7.83, 1.26 Hz, 1H) 7.82 (s, 1H) 8.01-8.03 (m, 1H).

Example 18

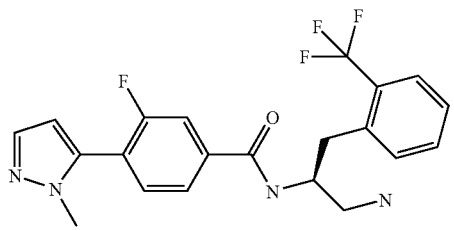

Preparation of N-((1S)-2-amino-1-{[2-(trifluoromethyl)phenyl]methyl}ethyl)-3-fluoro-4-(1-methyl-1H-pyrazol-5-yl)benzamide a). 3-fluoro-4-(1-methyl-1H-pyrazol-5-yl)benzoic acid

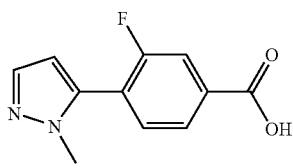

To a solution of 4-bromo-3-fluorobenzoic acid (110 mg, 0.5 mmol) in dioxane/H2O (5:1, 6 mL) was added K2CO3 (207 mg, 1.5 mmol), tetrakistriphenylphosphine Pd(0) (29 mg, 0.025 mmol) and 5-(5,5-dimethyl-1,3,2-dioxaborinan-2- yl)-1-methyl-1H-pyrazole (107 mg, 0.55 mmol). The reaction mixture was heated to 80° C. in a sealed tube for 12 h and was then partitioned between 6N NaOH and DCM. The pH of the aqueous phase was adjusted to ~3 with 3M HCl and washed several times with DCM. The combined organic fractions were dried (Na$_2$SO$_4$), concentrated under vacuum and used directly without further purification (98 mg, 89%): LC-MS (ES) m/z=221 (M+H)+.

b) N-((1S)-2-(1,3-dioxo-1,3-dihydro-2H-isoindol-2-yl)-1-{[2-(trifluoromethyl)phenyl]methyl}ethyl)-3-fluoro-4-(1-methyl-1H-pyrazol-5-yl)benzamide

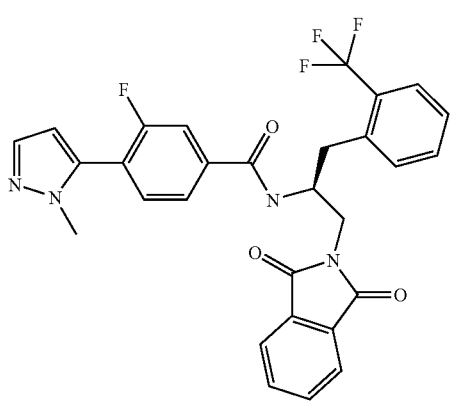

To a solution of 3-fluoro-4-(1-methyl-1H-pyrazol-5-yl)benzoic acid (66 mg, 0.3 mmol), PyBrOP (169 mg, 0.37 mmol) and diisopropylethyl amine (263 µL, 1.5 mmol) in DCM (3 mL) at 25° C. was added 2-{(2S)-2-amino-3-[2-(trifluoromethyl)phenyl]propyl}-1H-isoindole-1,3(2H)-dione-HCl (105 mg, 0.3 mmol)[prepared according to Preparation 3]. After 16 h, the solution was partitioned between H$_2$O and washed with DCM. The combined organic fractions were dried (Na$_2$SO$_4$), concentrated and purified via column chromatography (silica) affording the title compound (112 mg, 68%) as a white solid: LC-MS (ES) m/z=551 (M+H)+.

c) N-((1S)-2-amino-1-{[2-(trifluoromethyl)phenyl]methyl}ethyl)-3-fluoro-4-(1-methyl-1H-pyrazol-5-yl)benzamide To a solution of N-((1S)-2-(1,3-dioxo-1,3-dihydro-2H-isoindol-2-yl)-1-{[2-(trifluoromethyl)phenyl]methyl}ethyl)-3-fluoro-4-(1-methyl-1H-pyrazol-5-yl)benzamide (112 mg, 0.2 mmol) in MeOH/THF (2 mL, 1:1) at RT was added hydrazine (0.12 mL, 3.93 mmol). After stirring for 18 h at RT, the reaction solution was concentrated under vacuum and purified via column chromatography (silica, 3% MeOH in DCM (1% NH4OH)) yielding the title compound.

The neutral compound from above was dissolved in MeOH (2 mL), treated with excess 4M HCl in dioxane (0.5 mL) and concentrated affording the HCl salt of the title compound as a white solid: LC-MS (ES) m/z 421 (M+H)$^+$, $^1$H NMR (400 MHz, MeOD) δ ppm 3.12-3.20 (m, 1H) 3.24-3.32 (m, 3H) 3.86 (d, J=1.26 Hz, 3 H) 4.72-4.79 (m, 1H) 6.55 (d, J=2.02 Hz, 1H) 7.41-7.48 (m, 1H) 7.52-7.58 (m, 2H) 7.58-7.63 (m, 1H) 7.70-7.74 (m, 2H) 7.74-7.82 (m, 2H).

Example 19

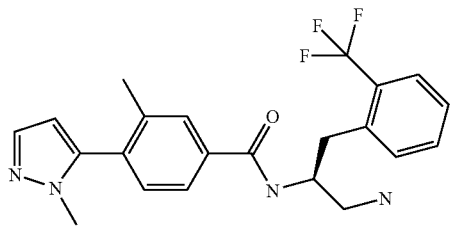

Preparation of N-((1S)-2-amino-1-{[2-(trifluoromethyl)phenyl]methyl}ethyl)-3-methyl-4-(1-methyl-1H-pyrazol-5-yl)benzamide The title compound was prepared as a white solid according to the procedure of Example 18, except substituting 4-bromo-3-methylbenzoic acid (109 mg, 0.5 mmol) for 4-bromo-3-fluorobenzoic acid: LC-MS (ES) m/z 417 (M+H)$^+$, $^1$H NMR (400 MHz, MeOD) δ ppm 2.24 (s, 3H) 3.09-3.17 (m, 1H) 3.21-3.29 (m, 3 H) 3.65 (s, 3H) 4.73 (s, 1H) 6.31-6.32 (m, 1H) 7.37 (d, J=8 Hz, 1H) 7.44-7.47 (m, 1H) 7.52-7.59 (m, 3H) 7.69-7.75 (m, 2H) 7.78-7.80 (m, 1H).

Example 20

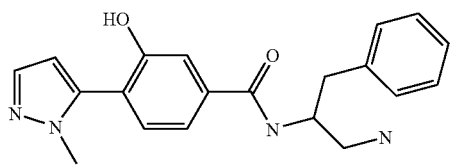

Preparation of N-[2-amino-1-(phenylmethyl)ethyl]-3-hydroxy-4-(1-methyl-1H-pyrazol-5-yl)benzamide The title compound was prepared as a yellow solid according to the procedure of Example 3, except substituting 4-bromo-3-hydroxybenzoic acid (108 mg, 0.5 mmol) for 5-bromo-2-pyrimidinecarboxylic acid: LC-MS (ES) m/z 351 (M+H)$^+$, $^1$H NMR (400 MHz, MeOD) δ ppm 3.01 (s, 2H) 3.18 (s, 2H) 3.76 (s, 3 H) 4.60 (s, 1H) 6.35 (s, 2H) 7.25 (s, 1H) 7.30 (s, 2H) 7.32 (s, 4H) 7.37 (s, 1H) 7.57 (s, 1H).

Example 21

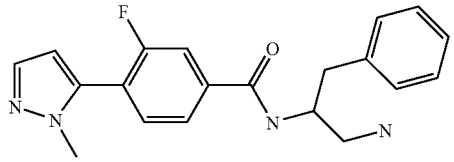

Preparation of N-[2-amino-1-(phenylmethyl)ethyl]-3-fluoro-4-(1-methyl-1H-pyrazol-5-yl)benzamide The title compound was prepared as a white solid according to Example 3, except substituting 4-bromo-3-fluorobenzoic acid (110 mg, 0.5 mmol) for 5-bromo-2-pyrimidinecarboxylic acid: LC-MS (ES) m/z 421 (M+H)+, 1H NMR (400 MHz, MeOD) δ ppm 3.06 (d, J=7.07 Hz, 2H) 3.23-3.30 (m, 2H) 4.02 (s, 3H) 4.60-4.68 (m, 1H) 6.89-6.91 (m, 1H) 7.24 (d, J=5.81 Hz, 1H) 7.28-7.36 (m, 4H) 7.71 (t, J=7.33 Hz, 1H) 7.77-7.87 (m, 2H) 8.22-8.32 (m, 1H).

Example 22

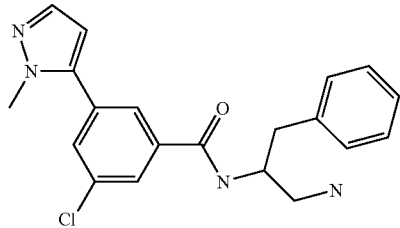

Preparation of N-[2-amino-1-(phenylmethyl)ethyl]-3-chloro-5-(1-methyl-1H-pyrazol-5-yl)benzamide The title compound was prepared as a white solid according to Example 3, except substituting 3-bromo-5-chlorobenzoic acid (282 mg, 1.2 mmol) for 5-bromo-2-pyrimidinecarboxylic acid: LC-MS (ES) m/z 369 (M+H)+, 1H NMR (400 MHz, MeOD) δ ppm 3.05 (d, J=7.83 Hz, 2H) 3.26 (d, J=6.57 Hz, 2H) 4.09 (s, 3H) 4.59-4.67 (m, J=7.14, 7.14, 7.14, 7.14 Hz, 1H) 6.92 (d, J=2.78 Hz, 1H) 7.23 (t, J=6.82 Hz, 1H) 7.28-7.36 (m, 4H) 7.86 (s, 1H) 8.00 (s, 2H) 8.20 (s, 1H).

Example 23

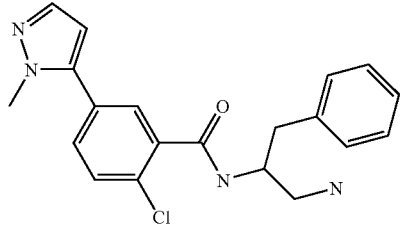

Preparation of N-[2-amino-1-(phenylmethyl)ethyl]-2-chloro-5-(1-methyl-1H-pyrazol-5-yl)benzamide The title compound was prepared as a white solid according to the procedure of Example 3, except substituting 5-bromo-2-chlorobenzoic acid (282 mg, 1.2 mmol) for 5-bromo-2-pyrimidinecarboxylic acid: LC-MS (ES) m/z 369 (M+H)+, 1H NMR (400 MHz, MeOD) δ ppm 2.93-3.02 (m, 1H) 3.04-3.11 (m, 1H) 3.15-3.27 (m, 2H) 4.04 (s, 3H) 4.60- 4.68 (m, 1H) 6.82 (s, 1H) 7.23-7.30 (m, 1H) 7.30-7.37 (m, 4H) 7.58-7.69 (m, 3H), 8.12 (s, 1H).

Example 24

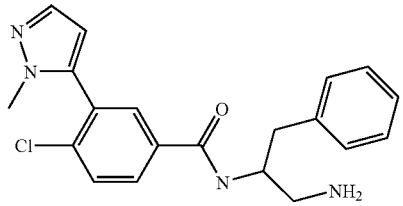

Preparation of N-[2-amino-1-(phenylmethyl)ethyl]-4-chloro-3-(1-methyl-1H-pyrazol-5-yl)benzamide The title compound was prepared as an off-white solid according to Example 3, except substituting 3-bromo-4-chlorobenzoic acid (282 mg, 1.2 mmol) for 5-bromo-2-pyrimidinecarboxylic acid: LC-MS (ES) m/z 369 (M+H)+, 1H NMR (400 MHz, MeOD) δ ppm 2.98-3.06 (m, 2H) 3.17-3.26 (m, 2H) 3.79-3.83 (m, 3H) 4.59 (s, 1H) 6.59 (d, J=2.27 Hz, 1H) 7.23 (dt, J=6.00, 2.94 Hz, 1H) 7.28-7.34 (m, 4H) 7.73 (d, J=8.59 Hz, 1H) 7.85-7.95 (m, 3H).

Example 25

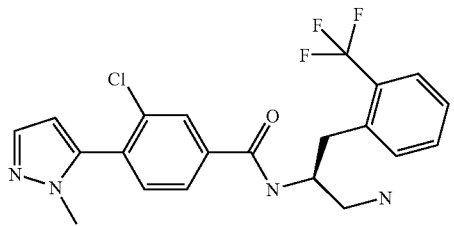

Preparation of N-((1S)-2-amino-1-{[2-(trifluoromethyl)phenyl]methyl}ethyl)-4-chloro-5-(1-methyl-1H-pyrazol-5-yl)-2-pyridinecarboxamide The title compound was prepared as a white solid according to Example 8, except substituting 5-bromo-4-chloro-2-pyridinecarboxylic acid (142 mg, 0.6 mmol)[prepared according to Example 10] for 4-bromo-3-fluorobenzoic acid: LC-MS (ES) m/z 438 (M+H)+, 1H NMR (400 MHz, MeOD) δ ppm 3.12-3.21 (m, 1H) 3.30 (d, J=4.04 Hz, 3H) 3.80 (s, 3H) 4.73 (d, J=4.55 Hz, 1H) 6.56-6.62 (m, 1H) 7.41 (t, J=7.07 Hz, 1H) 7.50 (t, J=7.33 Hz, 1H) 7.53-7.59 (m, 1H) 7.70 (d, J=7.83 Hz, 1H) 7.73-7.79 (m, 1H) 8.20 (s, 1H) 8.72 (s, 1H)

Example 26

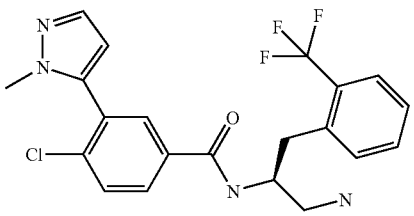

Preparation of N-((1S)-2-amino-1-{[2-(trifluoromethyl)phenyl]methyl}ethyl)-4-chloro-3-(1-methyl-1H-pyrazol-5-yl)benzamide The title compound was prepared as a white solid according to Example 18, except substituting 3-bromo-4-chlorobenzoic acid (282 g, 1.2 mmol) for 4-bromo-3-fluorobenzoic acid: LC-MS (ES) m/z 437 (M+H)+, $^1$H NMR (400 MHz, MeOD) δ ppm 3.18 (d, J=9.85 Hz, 1H) 3.22-3.31 (m, 3H) 3.91 (d, J=7.33 Hz, 3H) 4.70-4.76 (m, 1H) 6.65-6.78 (m, 1H) 7.43 (t, J=7.45 Hz, 1H) 7.50-7.58 (m, 2H) 7.71 (d, J=7.83 Hz, 1H) 7.77 (d, J=8.84 Hz, 1H) 7.98-8.08 (m, 3H).

Example 27

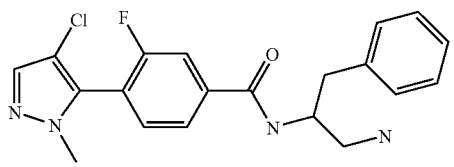

Preparation of N-[2-amino-1-(phenylmethyl)ethyl]-4-(4-chloro-1-methyl-1H-pyrazol-5-yl)-3-fluorobenzamide a) 3-fluoro-4-(1-methyl-1H-pyrazol-5-yl)benzoic acid

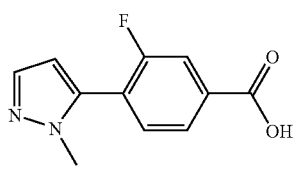

To a solution of 4-bromo-3-fluorobenzoic acid (220 mg, 1.0 mmol) in dioxane/H$_2$O (5:1, 12 mL) was added K$_2$CO$_3$ (414 mg, 3.0 mmol), tetrakistriphenylphosphine Pd(0) (58 mg, 0.05 mmol) and 5-(5,5-dimethyl-1,3,2-dioxaborinan-2-yl)-1-methyl-1H-pyrazole (214 mg, 1.1 mmol). The reaction mixture was heated to 80° C. in a sealed tube for 12 h and was then partitioned between 6N NaOH and DCM. The pH of the aqueous phase was adjusted to ~3 with 3M HCl and washed several times with DCM. The combined organic fractions were dried (Na$_2$SO$_4$), concentrated under vacuum and used directly without further purification (196 mg, 89%): LC-MS (ES) m/z=221 (M+H)+.

b) 4-(4-chloro-1-methyl-1H-pyrazol-5-yl)-3-fluorobenzoic acid

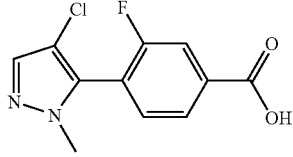

A solution of 3-fluoro-4-(1-methyl-1H-pyrazol-5-yl)benzoic acid (196 mg, 0.89 mmol) and N-chlorosuccinimide (119 mg, 0.89 mmol) in THF (5 mL) was stirred in a sealed tube at 70° C. After 1 h, the solution was partitioned between H$_2$O-DCM, the aqueous phase was adjusted to pH 3 and the aqueous phase was washed several times with DCM. The combined organic fractions were dried (Na$_2$SO$_4$), concentrated under vacuum and used directly without further purification (192 mg, 85%): LC-MS (ES) m/z=255 (M+H)+.

c). 1,1-dimethylethyl[2-({[4-(4-chloro-1-methyl-1H-pyrazol-5-yl)-3-fluorophenyl]carbonyl}amino)-3-phenylpropyl]carbamate

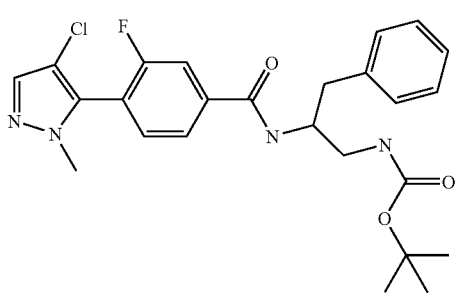

To a solution of 4-(4-chloro-1-methyl-1H-pyrazol-5-yl)-3-fluorobenzoic acid (100 mg, 0.43 mmol), 1,1-dimethylethyl (2-amino-3-phenylpropyl)carbamate (108 mg, 0.43 mmol), diisopropylethyl amine (0.4 mL, 2.14 mmol) in DCM (5 mL) was added PyBrop (330 mg, 0.71 mmol) in one portion. After 1 h, the reaction contents were partitioned between H$_2$O/DCM. The aqueous phase was washed several times with DCM. The combined organic fractions were dried (Na$_2$SO$_4$), concentrated and purified via column chromatography (silica) affording the title compound (79 mg, 38%) as a white solid: LCMS (ES) m/z=487 (M+H)+.

d) N-[2-amino-1-(phenylmethyl)ethyl]-4-(4-chloro-1-methyl-1H-pyrazol-5-yl)-3-fluorobenzamide A solution of 1,1-dimethylethyl[2-({[4-(4-chloro-1-methyl-1H-pyrazol-5-yl)-3-fluorophenyl]carbonyl}amino)-3-phenylpropyl]carbamate in TFA-DCM (3 mL, 1:2) was stirred at 25° C. After 30 min, the solution was concentrated and the residue neutralized through a silica plug (4% MeOH in DCM (1% NH$_4$OH)) affording the free base of the title compound.

The free base, as a solution in MeOH, was then treated with excess 4M HCl in dioxane affording a white solid as the HCl salt of the title compound (17 mg, 17%): LC-MS (ES) m/z 387 (M+H)+, 1H NMR (400 MHz, MeOD) δ ppm 3.01-3.07 (m, 2H) 3.18-3.29 (m, 2H) 3.73-3.79 (m, 3H) 4.61 (d, J=3.54 Hz, 1H) 7.26 (d, J=4.80 Hz, 1H) 7.34 (d, J=3.03 Hz, 4H) 7.57 (t, J=7.45 Hz, 1H) 7.60-7.66 (m, 1H) 7.71-7.80 (m, 2H).

Example 28

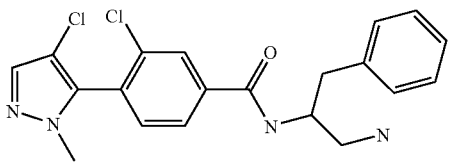

Preparation of N-[2-amino-1-(phenylmethyl)ethyl]-3-chloro-4-(4-chloro-1-methyl-1H-pyrazol-5-yl)benzamide The title compound was prepared as a white solid according to Example 27, except substituting 4-bromo-3-chlorobenzoic acid (282 g, 1.2 mmol) for 4-bromo-3-fluorobenzoic acid: LC-MS (ES) m/z 403 (M+H)+, 1H NMR (400 MHz, MeOD) δ ppm 2.99-3.10 (m, 2H) 3.19-3.29 (m, 2H) 3.69 (s, 3H) 4.59-4.67 (m, 1H) 7.22-7.28 (m, 1H) 7.30-7.36 (m, 4H) 7.52 (d, J=8.08 Hz, 1H) 7.59 (s, 1H) 7.88 (ddd, J=7.96, 3.92, 1.77 Hz, 1H) 8.02 (dd, J=4.17, 1.64 Hz, 1H).

Example 29

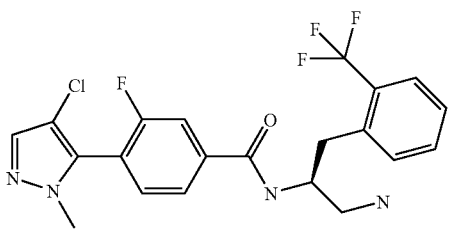

Preparation of N-((1S)-2-amino-1-{[2-(trifluoromethyl)phenyl]methyl}ethyl)-3-fluoro-4-(4-chloro-1-methyl-1H-pyrazol-5-yl)benzamide a). 3-fluoro-4-(1-methyl-1H-pyrazol-5-yl)benzoic acid

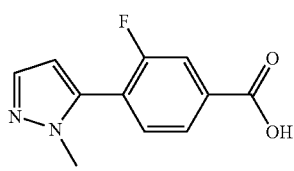

To a solution of 4-bromo-3-fluorobenzoic acid (220 mg, 1.0 mmol) in dioxane/H2O (5:1, 12 mL) was added K2CO3 (414 mg, 3.0 mmol), tetrakistriphenylphosphine Pd(0) (58 mg, 0.05 mmol) and 5-(5,5-dimethyl-1,3,2-dioxaborinan-2-yl)-1-methyl-1H-pyrazole (214 mg, 1.1 mmol). The reaction mixture was heated to 80° C. in a sealed tube for 12 h and was then partitioned between 6N NaOH and DCM. The pH of the aqueous phase was adjusted to ~3 with 3M HCl and washed several times with DCM. The combined organic fractions were dried (Na2SO4), concentrated under vacuum and used directly without further purification (196 mg, 89%): LC-MS (ES) m/z=221 (M+H)+.

b). 4-(4-chloro-1-methyl-1H-pyrazol-5-yl)-3-fluorobenzoic acid

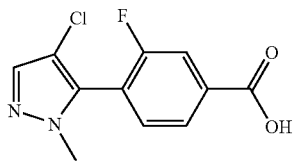

A solution of 3-fluoro-4-(1-methyl-1H-pyrazol-5-yl)benzoic acid (196 mg, 0.89 mmol) and N-chlorosuccinimide (119 mg, 0.89 mmol) in THF (5 mL) was stirred in a sealed tube at 70° C. After 1 h, the solution was partitioned between H2O-DCM, the aqueous phase was adjusted to pH 3 and the aqueous phase was washed several times with DCM. The combined organic fractions were dried (Na2SO4), concentrated under vacuum and used directly without further purification (192 mg, 85%): LC-MS (ES) m/z=255 (M+H)+.

c). 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-3-fluorobenzamide

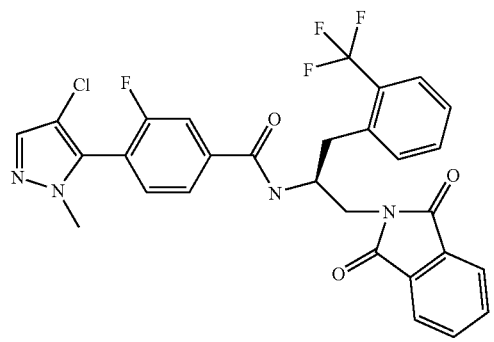

To a solution of 4-(4-chloro-1-methyl-1H-pyrazol-5-yl)-3-fluorobenzoic acid (100 mg, 0.43 mmol), 2-{(2S)-2-amino-3-[2-(trifluoromethyl)phenyl]propyl}-1H-isoindole-1,3 (2H)-dione-HCl (151 mg, 0.43 mmol) [prepared according to Preparation 3], diisopropylethyl amine (0.4 mL, 2.14 mmol) in DCM (5 mL) was added PyBrop (330 mg, 0.71 mmol) in one portion. After 1 h, the reaction contents were partitioned between H2O/DCM. The aqueous phase was washed several times with DCM. The combined organic fractions were dried (Na2SO4), concentrated and purified via column chromatography (silica) affording the title compound (90 mg, 36%) as a white solid: LCMS (ES) m/z=585 (M+H)+.

d) N-((1S)-2-amino-1-{[2-(trifluoromethyl)phenyl]methyl}ethyl)-3-fluoro-4-(4-chloro-1-methyl-1H-pyrazol-5-yl)benzamide To a solution of 4-(4-chloro-1-methyl-1H-pyrazol-5-yl)-N-((1S)-2-(1,3-dioxo-1,3-dihydro-2H-isoindol-2-yl)-1-{[2-(trifluoromethyl)phenyl]methyl}ethyl)-3-fluorobenzamide (90 mg, 0.15 mmol) in MeOH/THF (2 mL, 1:1) at RT was added hydrazine (0.12 mL, 3.93 mmol). After stirring for 18 h at RT, the reaction solution was concentrated under vacuum and purified via column chromatography (silica, 3% MeOH in DCM (1% NH4OH)) yielding the title compound (14 mg, 21%).

The neutral compound from above was dissolved in MeOH (2 mL), treated with excess 4M HCl in dioxane (0.5 mL) and concentrated affording the HCl salt of the title compound as a light yellow solid: LC-MS (ES) m/z 455 (M+H)$^+$, $^1$H NMR (400 MHz, MeOD) δ ppm 3.17 (d, J=9.09 Hz, 1H) 3.26 (d, J=6.32 Hz, 3H) 3.72-3.80 (m, 3H) 4.74 (s, 1H) 7.41-7.49 (m, 1H) 7.54-7.64 (m, 4H) 7.72-7.84 (m, 3H).

Example 30

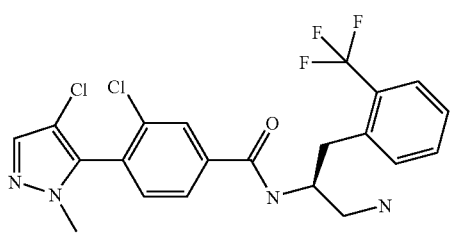

Preparation of N-((1S)-2-amino-1-{[2-(trifluoromethyl)phenyl]methyl}ethyl)-3-chloro-4-(4-chloro-1-methyl-1H-pyrazol-5-yl)benzamide The title compound was prepared as a white solid according to Example 29, except substituting 4-bromo-3-chlorobenzoic acid (282 mg, 1.2 mmol) for 4-bromo-3-fluorobenzoic acid: LC-MS (ES) m/z 471 (M+H)$^+$, $^1$H NMR (400 MHz, MeOD) δ ppm 3.20 (d, J=9.35 Hz, 1H) 3.28 (d, J=3.54 Hz, 2H) 3.37 (s, 1H) 3.70 (s, 3H) 4.75 (d, J=4.55 Hz, 1H) 7.41-7.47 (m, 1H) 7.55 (d, J=7.83 Hz, 2H) 7.59-7.62 (m, 2H) 7.72 (d, J=7.58 Hz, 1H) 7.96 (d, J=8.08 Hz, 1H) 8.09 (s, 1H).

Example 31

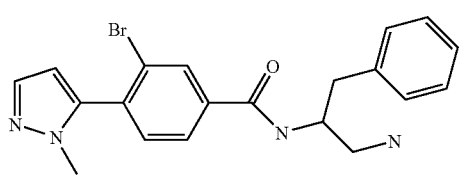

Preparation of N-[2-amino-1-(phenylmethyl)ethyl]-3-bromo-4-(1-methyl-1H-pyrazol-5-yl)benzamide a) methyl 3-bromo-4-(1-methyl-1H-pyrazol-5-yl)benzoate

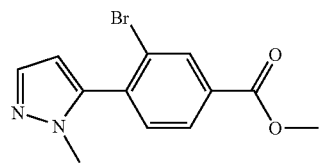

To a solution of methyl 3-bromo-4-iodobenzoate (409 mg, 1.2 mmol) in dioxane/H$_2$O (4:1, 10 mL) was added K$_2$CO$_3$ (497 mg, 3.6 mmol), tetrakistriphenylphosphine Pd(0) (69 mg, 0.06 mmol) and 5-(5,5-dimethyl-1,3,2-dioxaborinan-2-yl)-1-methyl-1H-pyrazole (349 mg, 3.6 mmol). The reaction mixture was heated to 80° C. in a sealed tube for 12 h and was then partitioned between 6N NaOH and DCM. The pH of the aqueous phase was adjusted to ~3 with 3M HCl and washed several times with DCM. The combined organic fractions were dried (Na$_2$SO$_4$), concentrated under vacuum and used directly without further purification (307 mg, 87%): LC-MS (ES) m/z=296 (M+H)+.

b) 3-bromo-4-(1-methyl-1H-pyrazol-5-yl)benzoic acid

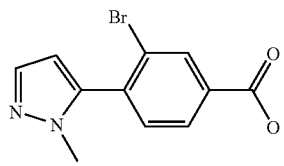

To a solution of methyl 3-bromo-4-(1-methyl-1H-pyrazol-5-yl)benzoate (275 mg, 093 mmol) in MeOH (10 mL) was added NaOH solution (2.5 M, 3.72 mL, 9.3 mmol). After 12 h at 25° C., the solution was partitioned between H$_2$O-DCM and the pH of the aqueous phase was adjusted to ~4 with 6N HCl solution. The aqueous phase was washed several times with DCM and the combined organic fractions were dried over Na$_2$SO$_4$ and concentrated to afford the title compound as a white solid (230.1 mg, 88%): LC-MS (ES) m/z=282 (M+H)+.

c) 1,1-dimethylethyl[2-({[3-bromo-4-(1-methyl-1H-pyrazol-5-yl)phenyl]carbonyl}amino)-3-phenylpropyl]carbamate

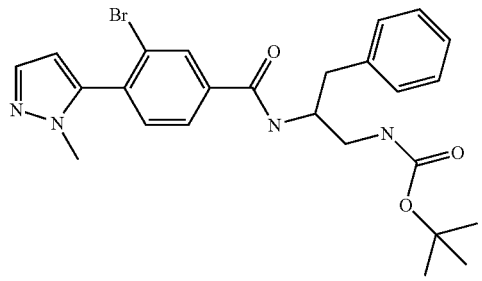

To a solution of 3-bromo-4-(1-methyl-1H-pyrazol-5-yl)benzoic acid (100 mg, 0.36 mmol), PyBrOP (277 mg, 0.59 mmol) and diisopropylethyl amine (0.11 mL, 0.59 mmol) in DCM (6 mL) at 25° C. was added 1,1-dimethylethyl (2-amino-3-phenylpropyl)carbamate (90 mg, 0.36 mmol) [prepared in Preparation 2]. After 16 h, the solution was concentrated and purified via column chromatography (silica, hexanes/EtOAc, 2:1) affording the title compound (87 mg, 47%) as a white solid: LC-MS (ES) m/z=514 (M+H)$^+$.

d) N-[2-amino-1-(phenylmethyl)ethyl]-3-bromo-4-(1-methyl-1H-pyrazol-5-yl)benzamide 1,1-dimethylethyl[2-({[3-bromo-4-(1-methyl-1H-pyrazol-5-yl)phenyl]carbonyl}amino)-3-phenylpropyl]carbamate (87 g, 0.17 mmol) was dissolved in MeOH (1 mL) and CHCl$_3$ (10 mL) and treated with 4M HCl in dioxane (5 mL). After 3 h, the solution was concentrated and purified via column chromatography (silica, CHCl$_3$/MeOH, 90:10 containing 1% NH$_4$OH affording the free base of the title compound (30.7 mg, 44%) as a white powder.

The free base, as a solution in MeOH (2 mL) was treated with an excess of 1M HCl in Et$_2$O affording the final compound as the HCl salt: LC-MS (ES) m/z 413(M+H)$^+$, $^1$H NMR (400 MHz, MeOD) δ ppm 2.98-3.08 (m, 2H) 3.14-3.29 (s, 2H) 3.70 (s, 3H) 4.63 (s, 1H) 6.38 (s, 1H) 7.25 (s, 1H) 7.33 (s, 4H) 7.50 (s, 1H) 7.60 (s, 1H) 7.84 (d, J=7.83 Hz, 1H) 8.12 (s, 1H).

Example 32

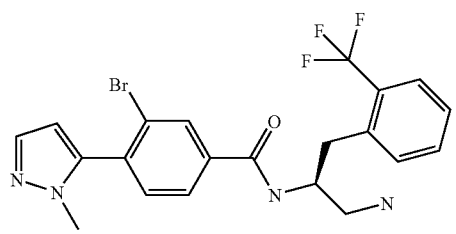

Preparation of N-((1S)-2-amino-1-{[2-(trifluoromethyl)phenyl]methyl}ethyl)-3-bromo-4-(1-methyl-1H-pyrazol-5-yl)benzamide a) methyl 3-bromo-4-(1-methyl-1H-pyrazol-5-yl)benzoate

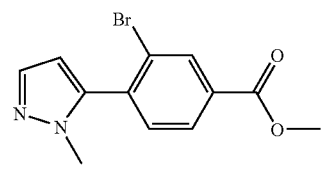

To a solution of methyl 3-bromo-4-iodobenzoate (409 mg, 1.2 mmol) in dioxane/H$_2$O (4:1, 10 mL) was added K$_2$CO$_3$ (497 mg, 3.6 mmol), tetrakistriphenylphosphine Pd(0) (69 mg, 0.06 mmol) and 5-(5,5-dimethyl-1,3,2-dioxaborinan-2-yl)-1-methyl-1H-pyrazole (349 mg, 3.6 mmol). The reaction mixture was heated to 80° C. in a sealed tube for 12 h and was then partitioned between 6N NaOH and DCM. The pH of the aqueous phase was adjusted to ~3 with 3M HCl and washed several times with DCM. The combined organic fractions were dried (Na$_2$SO$_4$), concentrated under vacuum and used directly without further purification (307 mg, 87%): LC-MS (ES) m/z=296 (M+H)$^+$.

b) 3-bromo-4-(1-methyl-1H-pyrazol-5-yl)benzoic acid

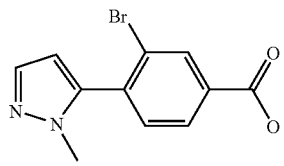

To a solution of methyl 3-bromo-4-(1-methyl-1H-pyrazol-5-yl)benzoate (275 mg, 0.93 mmol) in MeOH (10 mL) was added NaOH solution (2.5 M, 3.72 mL, 9.3 mmol). After 12 h at 25° C., the solution was partitioned between H$_2$O-DCM and the pH of the aqueous phase was adjusted to ~4 with 6N HCl solution. The aqueous phase was washed several times with DCM and the combined organic fractions were dried over Na$_2$SO$_4$ and concentrated to afford the title compound as a white solid (230.1 mg, 88%): LC-MS (ES) m/z=282 (M+H)$^+$.

c) 3-bromo-N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)benzamide

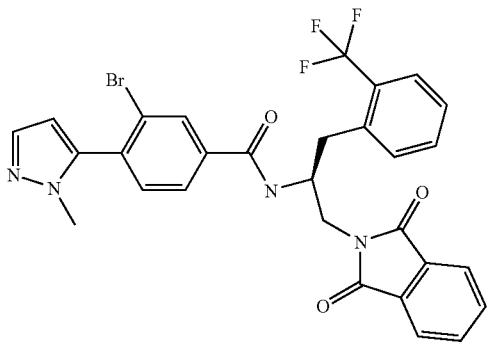

To a solution of 3-bromo-4-(1-methyl-1H-pyrazol-5-yl)benzoic acid (100 mg, 0.36 mmol), PyBrOP (277 mg, 0.59 mmol) and diisopropylethyl amine (0.11 mL, 0.59 mmol) in DCM (6 mL) at 25° C. was added 2-{(2S)-2-amino-3-[2-(trifluoromethyl)phenyl]propyl}-1H-isoindole-1,3(2H)-dione (161 mg, 0.36 mmol) [prepared according to Preparation 3]. After 16 h, the solution was concentrated and purified via column chromatography (silica, hexanes/EtOAc, 2:1) affording the title compound (172 mg, 78%) as a white solid: LC-MS (ES) m/z=612 (M+H)+.

d) N-((1S)-2-amino-1-{[2-(trifluoromethyl)phenyl]methyl}ethyl)-3-bromo-4-(1-methyl-1H-pyrazol-5-yl)benzamide To a solution of 3-bromo-N-((1S)-2-(1,3-dioxo-1,3-dihydro-2H-isoindol-2-yl)-1-{[2-(trifluoromethyl)phenyl]methyl}ethyl)-4-(1-methyl-1H-pyrazol-5-yl)benzamide (172 mg, 0.28 mmol) in MeOH/THF (4 mL, 1:1) at RT was added hydrazine (0.17 mL, 5.5 mmol). After stirring for 18 h at RT, the reaction solution was concentrated under vacuum and purified via column chromatography (silica, 3% MeOH in DCM (1% NH$_4$OH)) yielding the title compound (60.4 mg, 45%).

The neutral compound from above was dissolved in MeOH (2 mL), treated with excess 4M HCl in dioxane (500 μL) and concentrated affording the HCl salt of the title compound as a white solid: LC-MS (ES) m/z 482 (M+H)+, $^1$H NMR (400 MHz, MeOD) δ ppm 3.09-3.19 (m, 1H) 3.26 (d, J=6.32 Hz, 3H) 3.74 (s, 3H) 4.73 (s, 1H) 6.45 (s, 1H) 7.46 (s, 1H) 7.55 (t, J=3.79 Hz, 3H) 7.73 (d, J=7.83 Hz, 2H) 7.92 (s, 1H) 8.22 (s, 1H).

Example 33

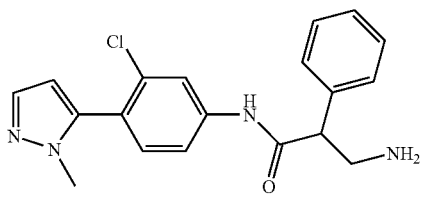

Preparation of 3-amino-N-[3-chloro-4-(1-methyl-1H-pyrazol-5-yl)phenyl]-2-phenylpropanamide a) 1,1-dimethylethyl{3-[(4-bromo-3-chlorophenyl)amino]-3-oxo-2-phenylpropyl}carbamate

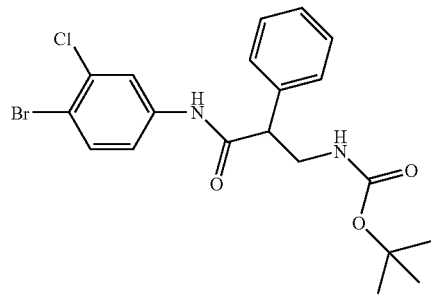

To a solution of 3-({[(1,1-dimethylethyl)oxy]carbonyl}amino)-2-phenylpropanoic acid (159 mg, 0.6 mmol), PyBrOP (462 mg, 0.99 mmol) and diisopropylethyl amine (0.35 mL, 2.0 mmol) in DCM (6 mL) at 25° C. was added 4-bromo-3-chloroaniline (124 mg, 0.6 mmol). After 16 h, the solution was concentrated and purified via column chromatography (silica, hexanes/EtOAc, 2:1) affording the title compound (248 mg, 91%) as a white solid: LC-MS (ES) m/z=454 (M+H)+.

b) 1,1-dimethylethyl(3-{[3-chloro-4-(1,3-dimethyl-1H-pyrrol-2-yl)phenyl]amino}-3-oxo-2-phenylpropyl)carbamate

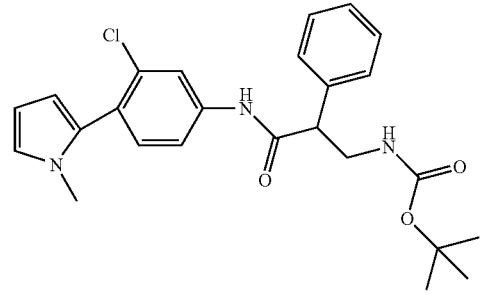

To a solution of 1,1-dimethylethyl(3-{[3-chloro-4-(1-methyl-1H-pyrrol-2-yl)phenyl]amino}-3-oxo-2-phenylpropyl)carbamate (247 mg, 0.54 mmol) in dioxane/H$_2$O (4:1, 10 mL) was added K$_2$CO$_3$ (224 mg, 1.62 mmol), tetrakistriphenylphosphine Pd(0) (31 mg, 0.03 mmol) and 5-(5,5-dimethyl-1,3,2-dioxaborinan-2-yl)-1-methyl-1H-pyrazole (157 mg, 1.62 mmol). The reaction mixture was heated to 80° C. in a sealed tube for 12 h and was then partitioned between H—$_2$O-DCM. The aqueous phase was washed several times with DCM and the combined organic fractions were dried (Na$_2$SO$_4$), concentrated under vacuum and used directly without further purification (228 mg, 93%): LC-MS (ES) m/z=455 (M+H)+.

c) 3-amino-N-[3-chloro-4-(1-methyl-1H-pyrazol-5-yl)phenyl]-2-phenylpropanamide 1,1-dimethylethyl (3-{[3-chloro-4-(1,3-dimethyl-1H-pyrrol-2-yl)phenyl]amino}-3-oxo-2-phenylpropyl)carbamate (228 mg, 0.5 mmol) was dissolved in MeOH (1 mL) and CHCl₃ (10 mL) and treated with 4M HCl in dioxane (5 mL). After 3 h, the solution was concentrated and purified via column chromatography (silica, CHCl₃/MeOH, 90:10 containing 1% NH₄OH) affording the free base of the title compound (146.4 mg, 83%) as a white powder.

The free base, as a solution in MeOH was treated with an excess of 1M HCl in Et₂O to yield the final compound as the HCl salt: LC-MS (ES) m/z 355 (M+H)⁺, ¹H NMR (400 MHz, MeOD) δ ppm 3.28 (dd, J=12.88, 5.31 Hz, 1H) 3.59-3.70 (m, 1 H) 3.87 (d, J=11.37 Hz, 3H) 4.22 (d, J=2.27 Hz, 1H) 6.67 (s, 1H) 7.39-7.50 (m, 6 H) 7.67 (s, 1H) 8.14 (d, J=5.05 Hz, 2H).

Example 34

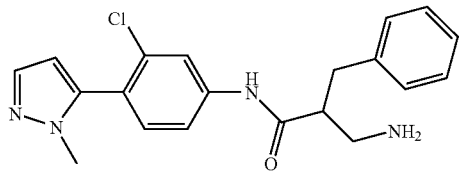

Preparation of 3-amino-N-[3-chloro-4-(1-methyl-1H-pyrazol-5-yl)phenyl]-2-(phenylmethyl)propanamide The title compound was prepared as a white solid according to Example 33, except substituting 3-({[(1,1-dimethylethyl)oxy]carbonyl}amino)-2-(phenylmethyl)propanoic acid (168 mg, 0.6 mmol)[prepared according to Preparation 5] for 3-({[(1,1-dimethylethyl)oxy]carbonyl}amino)-2-phenylpropanoic acid: LC-MS (ES) m/z 355 (M+H)⁺, ¹H NMR (400 MHz, MeOD) δ ppm 2.97 (dd, J=13.52, 7.20 Hz, 1H) 3.07 (dd, J=12.51, 3.41 Hz, 1H) 3.11-3.18 (m, 1H) 3.27 (s, 1H) 3.34-3.39 (m, 1H) 3.88 (s, 3H) 6.71 (s, 1H) 7.25 (d, J=4.29 Hz, 1H) 7.32 (d, J=4.04 Hz, 4H) 7.46 (d, J=8.59 Hz, 1H) 7.62-7.66 (m, 1H) 8.08 (d, J=1.77 Hz, 1H) 8.11 (s, 1H).

Example 35

Preparation of 3-amino-N-[3-(1-methyl-1H-pyrazol-5-yl)phenyl]-2-(phenylmethyl)propanamide

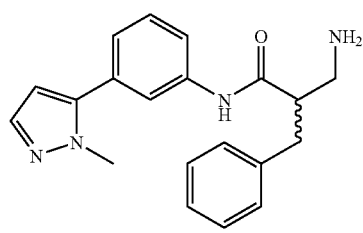

a) 1,1-dimethylethyl[3-[(3-bromophenyl)amino]-3-oxo-2-(phenylmethyl)propyl]carbamate

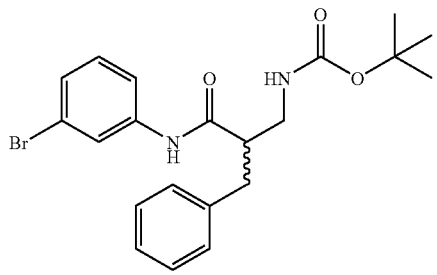

To a solution of 3-({[(1,1-dimethylethyl)oxy]carbonyl}amino)-2-(phenylmethyl)propanoic acid (360 mg, 1.29 mmol), PyBrOP (900 mg, 1.93 mmol) and diisopropylethyl amine (0.9 mL, 5 mmol) in DCM (10 mL) at 25° C. was added 3-bromoaniline (0.29 mg, 1.66 mmol). After 2 h, the solution was concentrated and purified via column chromatography (silica, hexanes/EtOAc, 10:1 to 3:1) affording the title compound (400 mg, 72%) as a white solid: LC-MS (ES) m/z=434 (M+H)⁺.

b) 1,1-dimethylethyl[3-{[3-(1-methyl-1H-pyrazol-5-yl)phenyl]amino}-3-oxo-2-(phenylmethyl)propyl]carbamate

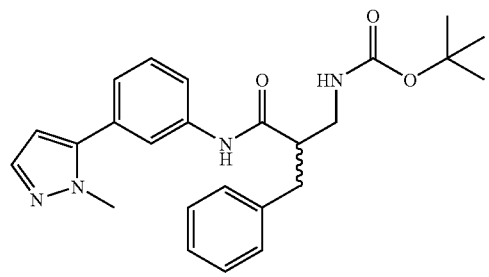

To a solution of 1,1-dimethylethyl[3-[(3-bromophenyl)amino]-3-oxo-2-(phenylmethyl)propyl]carbamate (230 mg, 0.53 mmol) in dioxane/H₂O (5:1, 6 mL) was added K₂CO₃ (220 mg, 1.59 mmol), tetrakistriphenylphosphine Pd(0) (61 mg, 52 μmol) and 1-methyl-5-(4,4,5,5-tetramethyl-1,3,2-dioxaborolan-2-yl)-1H-pyrazole (164 mg, 0.79 mmol). The reaction mixture was heated to 70° C. in a sealed tube. After 10 h, the reaction mixture was concentrated under vacuum and purified on silica (hexanes/EtOAc, 30-60%) to afford the title compound (0.17 g, 74%) as a light yellow solid: LC-MS (ES) m/z=435 (M+H)⁺.

c) 3-amino-N-[3-(1-methyl-1H-pyrazol-5-yl)phenyl]-2-(phenylmethyl)propanamide

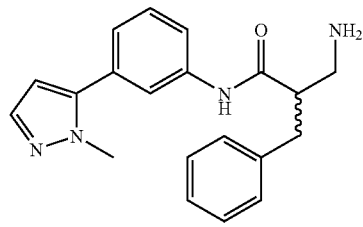

1,1-dimethylethyl[3-{[3-(1-methyl-1H-pyrazol-5-yl)phenyl]amino}-3-oxo-2-(phenylmethyl)propyl]carbamate (170 mg, 0.39 mmol) was dissolved in DCM (10 mL) and treated with TFA (1 mL). After 1 h, the solution was concentrated and purified using reverse-phase HPLC (C18 column: $H_2O$/$CH_3CN$, 40-10%) affording the bis-TFA salt of the title compound (115 mg, 52%) as a white solid. LC-MS (ES) m/z=335 (M+H)$^+$, $^1$H NMR (d4-MeOD, 400 MHz) δ 7.76 (br s, 1H), 7.43 (br s, 1 h), 7.35-7.23 (m, 9H), 4.55 (m, 1H), 3.72 (s, 3H), 3.23 (dd, J=3.5, 13.1 Hz, 1H), 3.13 (dd, J=10.4, 13.1 Hz, 1H), and 3.03-2.95 (m, 2H).

Example 36

Preparation of N-((1S)-2-amino-1-{[2-(trifluoromethyl)phenyl]methyl}ethyl)-4-(1-methyl-1H-1,2,4-triazol-5-yl)benzamide

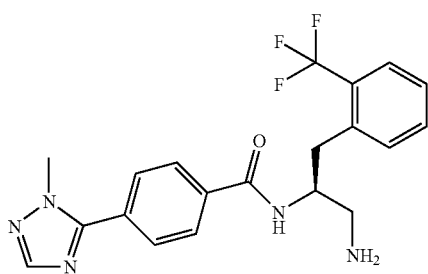

a) 4-(1-methyl-1H-1,2,4-triazol-5-yl)benzoic acid

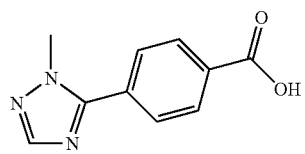

A mixture of 5-iodo-1-methyl-1H-1,2,4-triazole (418 mg, 2.00 mmol), {4-[(ethyloxy)carbonyl]phenyl}boronic acid (466 mg, 2.40 mmol), and BIS(TRIPHENYLPHOSPHINE) PALLADIUM(II) CHLORIDE (70.2 mg, 0.10 mmol) in tetrahydrofuran (THF) (10 mL) was stirred under $N_2$ in a 25 mL microwave reaction vessel. Sodium carbonate (1000 µl, 2.00 mmol) was added. The reaction mixture was purged with $N_2$, sealed and irradiated with MW at 138° C. for 28 min. The crude reaction mixture was loaded directly on a 25M biotage column, which was eluted with 50-100% of EtOAc/hexane to give the ester intermediate. This ester was hydrolyzed with 2N NaOH (4 mL) in THF (8 mL) at 70° C. The reaction was completed in one hour.

The organic layer was washed with $H_2O$ 3× and discarded. The combined aqueous layers were acidified with 2N HCl. The product had poor solubility, and it was extracted with MeOH/CHCl$_3$ 5×. The combined extracts were dried, and concentrated to give 0.36 g of light yellow solid (89%). LC-MS (ES) m/z=204 (M+H)$^+$.

b) N-((1S)-2-(1,3-dioxo-1,3-dihydro-2H-isoindol-2-yl)-1-{[2-(trifluoromethyl)phenyl]methyl}ethyl)-4-(1-methyl-1H-1,2,4-triazol-5-yl)benzamide

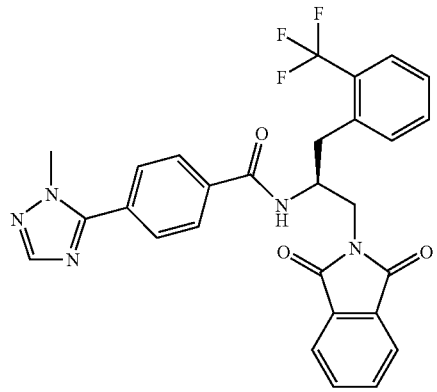

Hunig's base (0.084 ml, 0.48 mmol) was added to a suspension of 4-(1-methyl-1H-1,2,4-triazol-5-yl)benzoic acid (39.3 mg, 0.19 mmol), 2-{(2S)-2-amino-3-[2-(trifluoromethyl)phenyl]propyl}-1H-isoindole-1,3(2H)-dione (62 mg, 0.16 mmol), and PyBroP (75 mg, 0.16 mmol) in DCM (1 ml). The reaction mixture became clear and was stirred at RT overnight. The reaction mixture was loaded directly on a 25S Biotage column, which was eluted with 50-100% EA/DCM to give 67.3 mg of product. LC-MS (ES) m/z=534 (M+H)$^+$.

c) N-((1S)-2-amino-1-{[2-(trifluoromethyl)phenyl]methyl}ethyl)-4-(1-methyl-1H-1,2,4-triazol-5-yl)benzamide

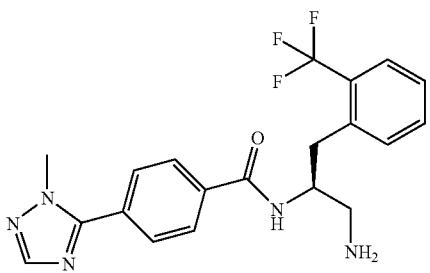

Hydrazine hydrate (0.028 ml, 0.58 mmol) was added to a solution of N-((1S)-2-(1,3-dioxo-1,3-dihydro-2H-isoindol-2-yl)-1-{[2-(trifluoromethyl)phenyl]methyl}ethyl)-4-(1-methyl-1H-1,2,4-triazol-5-yl)benzamide (67.3 mg, 0.116 mmol) in DCM/MeOH (1/0.1 ml).

The reaction mixture was stirred at RT overnight. A white precipitate formed. The reaction mixture was filtered through a syringe filter, concentrated and purified by RP-HPLC. The fractions containing product were concentrated and treated with 2N HCl aq. solution 3× to give product (19.3 mg, 36%) as a white solid. LC-MS (ES) m/z=404 (M+H)+, 1H NMR (d4-MeOD, 400 MHz) δ 8.74 (s, 1H), 8.13 (m, 2H), 7.95 (m, 2H), 7.72 (m, 1H), 7.60-7.51 (m, 2H), 7.44 (m, 1H), 4.71 (m, 1H), 4.15 (s, 3H), 3.35-3.15 (m, 4H).

Example 37

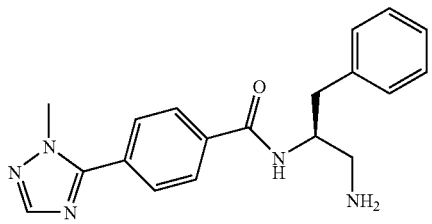

Preparation of N-[(1S)-2-amino-1-(phenylmethyl) ethyl]-4-(1-methyl-1H-1,2,4-triazol-5-yl)benzamide The title compound was prepared as a white solid according to Example 36, except substituting 2-[(2S)-2-amino-3-phenylpropyl]-1H-isoindole-1,3(2H)-dione [prepared according to Preparation 3] for 2-{(2S)-2-amino-3-[2-(trifluoromethyl)phenyl]propyl}-1H-isoindole-1,3(2H)-dione: LC-MS (ES) m/z 336 (M+H)+, 1H NMR (400 MHz, MeOD) δ ppm 8.82 (s, 1H), 8.09-8.07 (m, 2H), 7.95-7.92 (m, 2H), 7.35-7.23 (m, 5H), 4.65 (m, 1H), 4.15 (s, 3H), 3.3-3.0 (m, 4H).

Example 38

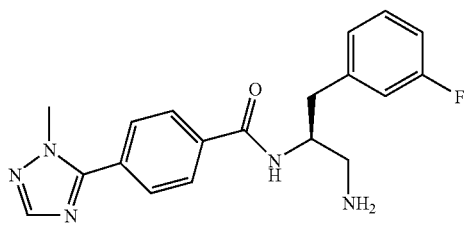

Preparation of N-{(1S)-2-amino-1-[(3-fluorophenyl) methyl]ethyl}-4-(1-methyl-1H-1,2,4-triazol-5-yl) benzamide The title compound was prepared as a white solid according to Example 36, except substituting 2-[(2S)-2-amino-3-(3-fluorophenyl)propyl]-1H-isoindole-1,3(2H)-dione [prepared according to Preparation 3] for 2-{(2S)-2-amino-3-[2-(trifluoromethyl)phenyl]propyl}-1H-isoindole-1,3(2H)-dione: LC-MS (ES) m/z 354 (M+H)+, 1H NMR (400 MHz, MeOD) δ ppm 8.91 (s, 1H), 8.12-8.10 (m, 2H), 7.31 (m, 1H), 7.18-7.10 (m, 2H), 6.96 (m, 1H), 4.65 (m, 1H), 4.16 (s, 3H), 3.3-3.0 (m, 4H).

Example 39

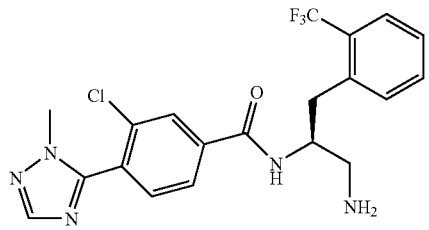

Preparation of N-((1S)-2-amino-1-{[2-(trifluoromethyl)phenyl]methyl}ethyl)-3-chloro-4-(1-methyl-1H-1,2,4-triazol-5-yl)benzamide The title compound was prepared as a white solid according to Example 36, except substituting {2-chloro-4-[(methyloxy)carbonyl]phenyl}boronic acid for {4-[(ethyloxy)carbonyl]phenyl}boronic acid: LC-MS (ES) m/z 404.2 (M+H)+, 1H NMR (d4-MeOH, 400 MHz) δ 8.38 (m, 1H), 8.11 (m, 1H), 7.96 (m, 1H), 7.73 (m, 2H), 7.56 (m, 2H), 7.45 (m, 1H), 4.76 (m, 1H), 3.88 (s, 3H), 3.26 (m, 2H), 3.16 (m, 2H).

Example 40

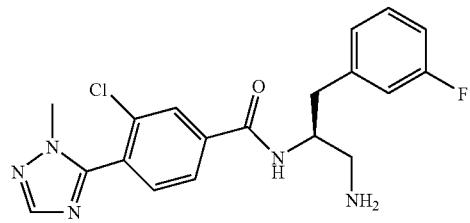

Preparation of N-{(1S)-2-amino-1-[(3-fluorophenyl) methyl]ethyl}-3-chloro-4-(1-methyl-1H-1,2,4-triazol-5-yl)benzamide The title compound was prepared as a white solid according to Example 38, except substituting {2-chloro-4-[(methyloxy)carbonyl]phenyl}boronic acid for {4-[(ethyloxy)carbonyl]phenyl}boronic acid: LC-MS (ES) m/z 388.2 (M+H)+, 1H NMR (400 MHz, MeOD) δ ppm 8.13 (m, 1H) 8.01 (s, 1H) 7.87 (d, 1H), 7.66 (d, 1H) 7.33 (m, 1H) 7.15-6.98 (m, 3H) 4.65 (m, 1H) 3.80 (s, 3H) 3.23 (m, 2H) 3.05 (m, 2H).

Example 41

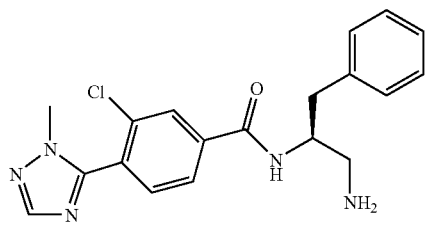

Preparation of N-[(1S)-2-amino-1-(phenylmethyl) ethyl]-3-chloro-4-(1-methyl-1H-1,2,4-triazol-5-yl) benzamide The title compound was prepared as a white solid according to Example 37, except substituting {2-chloro-4-[(methyloxy)carbonyl]phenyl}boronic acid for {4-[(ethyloxy)carbonyl]phenyl}boronic acid: LC-MS (ES) m/z 370 (M+H)+, 1H NMR (400 MHz, MeOD) δ ppm 8.65 (s, 1H), 8.09 (d, J=1 Hz, 1H), 7.96 (dd, J=8, 1 Hz, 1H), 7.79 (d, J=8 Hz, 1H), 7.34-7.24 (m, 5H), 4.62 (m, 1H), 4.16 (s, 3H), 3.3-3.0 (m, 4H).

Example 42

Preparation of N-((1S)-2-amino-1-{[2-(trifluoromethyl)phenyl]methyl}ethyl)-4-(1-methyl-1H-1,2,3-triazol-5-yl)benzamide

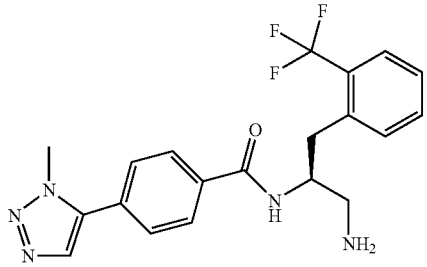

a) 4-(1-methyl-1H-1,2,3-triazol-5-yl)benzoic acid

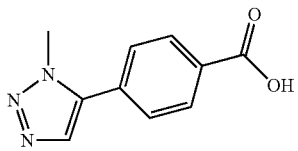

Triethylamine (0.28 ml, 2.00 mmol) was added to a mixture of 1-methyl-5-(tributylstannanyl)-1H-1,2,3-triazole (781 mg, 2.1 mmol), methyl 4-bromobenzoate (430 mg, 2.0 mmol), and BIS(TRIPHENYLPHOSPHINE)PALLADIUM (II) CHLORIDE (70.2 mg, 0.10 mmol) in toluene (10 ml) to give a yellow suspension. The reaction mixture was purged with N2, sealed and stirred at 100° C. for 3 hr. Potassium fluoride (465 mg, 8.00 mmol) and MeOH (2 mL) were added. The mixture was stirred at RT for 2 h, filtered on celite, and rinsed with EtOAc. The combined filtrates were concentrated and the residue was purified on a 25M biotage column to give 0.5 g of methyl 4-(1-methyl-1H-1,2,3-triazol-5-yl)benzoate as a tan solid.

A mixture of methyl 4-(1-methyl-1H-1,2,3-triazol-5-yl)benzoate (0.5 g, 2.30 mmol) and Sodium hydroxide (4.60 ml, 9.21 mmol, 2N aqueous solution) in tetrahydrofuran (THF) was heated at 70° C. for 1 hr. The organic layer was washed with H2O 3× and discarded. The combined aqueous layers were acidified with 2N HCl aqueous solution. The product precipitated and was filtered, rinsed with H2O and dried under vacuum to give 0.3 g (74%) as a tan solid. LC-MS (ES) m/z=204 (M+H)+.

b) N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)benzamide

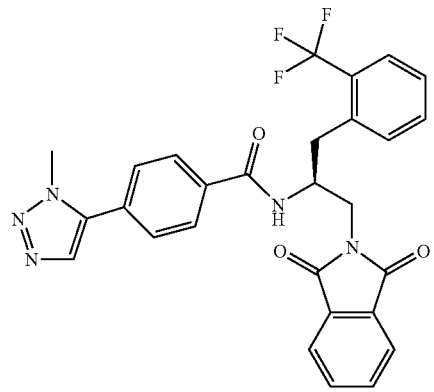

The title compound was prepared according to procedure 36(b) except substituting 4-(1-methyl-1H-1,2,3-triazol-5-yl) benzoic acid for 4-(1-methyl-1H-1,2,4-triazol-5-yl)benzoic acid: LC-MS (ES) m/z=534 (M+H)+.

c) N-((1S)-2-amino-1-{[2-(trifluoromethyl)phenyl]methyl}ethyl)-4-(1-methyl-1H-1,2,3-triazol-5-yl) benzamide

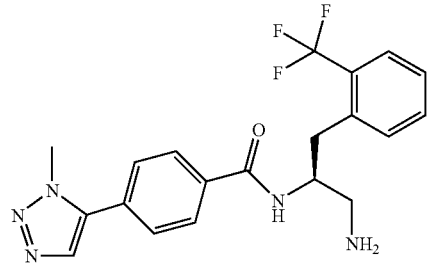

The title compound was prepared according to procedure 36(c) except substituting N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)benzamide for N-((1S)-2-(1,3-dioxo-1,3-dihydro-2H-isoindol-2-yl)-1-{[2-(trifluoromethyl)phenyl]methyl}ethyl)-4-(1-methyl-1H-1,2,4-triazol-5-yl)benzamide: LC-MS (ES) m/z=404 (M+H)+, 1H NMR (d4-MeOD, 400 MHz) δ 8.34 (s, 1H), 8.05-8.02 (m, 2H), 7.78-7.71 (m, 3H), 7.58-7.52 (m, 2H), 7.43 (m, 1H), 4.73 (m, 1H), 4.26 (s, 3H), 3.3-3.1 (m, 4H).

Example 43

Preparation of N-((1S)-2-amino-1-{[2-(trifluoromethyl)phenyl]methyl}ethyl)-4-(4-chloro-1-methyl-1H-1,2,3-triazol-5-yl)benzamide

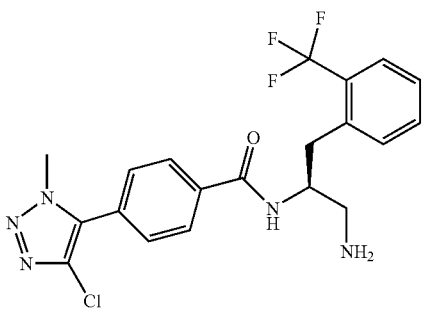

A mixture of N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)benzamide (0.1 g, 0.16 mmol) and NCS (0.043 g, 0.32 mmol) in DMF (1 mL) was heated at 50° C. for 2 hr. The reaction mixture was diluted with EtOAc, washed with H$_2$O 3×, dried and concentrated to give the crude product.

The crude chlorotriazole was dissolved in MeOH (0.1 mL) and DCM (1 mL). Hydrazine hydrate (0.04 ml, 0.80 mmol) was added. The reaction mixture was stirred at RT overnight. A white precipitate formed and was filtered through a syringe filter. The filtrates were concentrated and the residue was purified by RP-HPLC. The product fractions were concentrated and treated with 2N HCl aq., which was concentrated to give 65.8 mg of product as a light yellow solid. LC-MS (ES) m/z=438.2 (M+H)$^+$, $^1$H NMR (d4-MeOD, 400 MHz) δ ppm 8.34 (s, 1H), 8.02 (m, 2H), 7.74-7.68 (m, 3H), 7.56 (m, 2H), 7.43 (m, 1H), 4.73 (m, 1H), 4.08 (s, 3H), 3.36-3.12 (m, 4H).

Example 44

Preparation of N-[(1S)-2-amino-1-(phenylmethyl)ethyl]-4-(4-chloro-1-methyl-1H-1,2,3-triazol-5-yl)benzamide

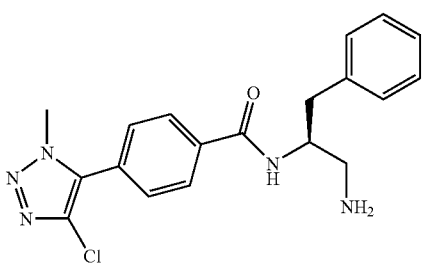

The title compound was prepared as a white solid according to the procedure of Example 43, except substituting N-((1S)-2-(1,3-dioxo-1,3-dihydro-2H-isoindol-2-yl)-1-[(2-phenyl)methyl]ethyl)-4-(1-methyl-1H-1,2,3-triazol-5-yl)benzamide for N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)benzamide: LC-MS (ES) m/z 370.2 (M+H)$^+$, $^1$H NMR (400 MHz, MeOD) δ ppm 7.98 (m, 2), 7.66 (m, 2H), 7.34-7.23 (m, 5H), 7.33 (m, 1H), 4.63 (m, 1H), 4.07 (s, 3H) 3.3-3.0 (m, 4H).

Example 45

Preparation of N-{(1S)-2-amino-1-[(3-fluorophenyl)methyl]ethyl}-4-(4-chloro-1-methyl-1H-1,2,3-triazol-5-yl)benzamide

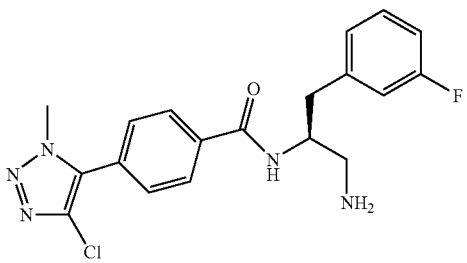

The title compound was prepared as a white solid according to the procedure of Example 43, except substituting N-{(1S)-2-(1,3-dioxo-1,3-dihydro-2H-isoindol-2-yl)-1-[(3-fluorophenyl)methyl]ethyl}-4-(1-methyl-1H-1,2,3-triazol-5-yl)benzamide for N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)benzamide. The title compound was a TFA salt: LC-MS (ES) m/z 388.2 (M+H)$^+$, $^1$H NMR (400 MHz, MeOD) δ ppm 7.95 (m, 2H), 7.68 (m, 2H), 7.34 (m, 1H), 7.15-7.07 (m, 2H), 6.98 (m, 1H), 4.63 (m, 1H), 4.07 (s, 3H), 3.29-2.95 (m, 4H).

Example 46

Preparation of N-[(1S)-2-amino-1-(phenylmethyl)ethyl]-4-(1-methyl-1H-1,2,3-triazol-5-yl)benzamide

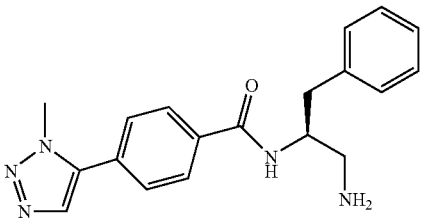

The title compound was prepared as a white solid according to the procedure of Example 42, except substituting N-((1S)-2-(1,3-dioxo-1,3-dihydro-2H-isoindol-2-yl)-1-[(2-phenyl)methyl]ethyl)-4-(1-methyl-1H-1,2,3-triazol-5-yl)benzamide for N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)benzamide: LC-MS (ES) m/z 336.2 (M+H)$^+$, $^1$H NMR (400 MHz, MeOD) δ ppm 8.65 (s, 1H), 8.02 (m, 2H), 7.80 (m, 2H), 7.36-7.22 (m, 5H), 4.64 (m, 1H), 4.32 (s, 3H), 3.3-3.0 (m, 4H).

Example 47

Preparation of N-{(1S)-2-amino-1-[(3-fluorophenyl)methyl]ethyl}-4-(1-methyl-1H-1,2,3-triazol-5-yl)benzamide

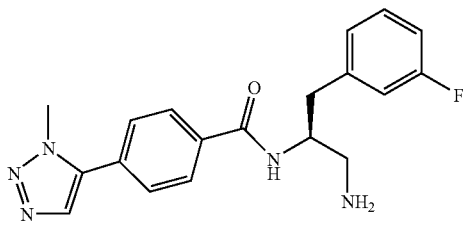

The title compound was prepared as a white solid according to the procedure of Example 43, except substituting N-{(1S)-2-(1,3-dioxo-1,3-dihydro-2H-isoindol-2-yl)-1-[(3-fluorophenyl)methyl]ethyl}-4-(1-methyl-1H-1,2,3-triazol-5-yl)benzamide for N-((1S)-2-(1,3-dioxo-1,3-dihydro-2H-isoindol-2-yl)-1-{[2-(trifluoromethyl)phenyl]methyl}ethyl)-4-(1-methyl-1H-1,2,3-triazol-5-yl)benzamide. The title compound was a TFA salt: LC-MS (ES) m/z 354.2 (M+H)+, $^1$H NMR (400 MHz, MeOD) δ ppm 7.94-7.90 (m, 3H), 7.69 (m, 2H), 7.33 (m, 1H) 7.15-7.07 (m, 2H), 6.98 (m, 1H), 4.62 (m, 1H), 4.15 (s, 3H), 3.30-2.96 (m, 4H).

Example 48

Capsule Composition

An oral dosage form for administering the present invention is produced by filing a standard two piece hard gelatin capsule with the ingredients in the proportions shown in Table I, below.

TABLE I

| INGREDIENTS | AMOUNTS |
| --- | --- |
| N-[2-amino-1-(phenylmethyl)ethyl]-5-(1-methyl-1H-pyrazol-5-yl)-2-pyridinecarboxamide (Compound of Example 1) | 25 mg |
| Lactose | 55 mg |
| Talc | 16 mg |
| Magnesium Stearate | 4 mg |

Example 49

Injectable Parenteral Composition

An injectable form for administering the present invention is produced by stirring 1.5% by weight of N-[2-amino-1-(phenylmethyl)ethyl]-6-(1-methyl-1H-pyrazol-5-yl)-3-pyridinecarboxamide (compound of Example 2), in 10% by volume propylene glycol in water.

Example 50

Tablet Composition

The sucrose, calcium sulfate dihydrate and an Akt inhibitor as shown in Table II below, are mixed and granulated in the proportions shown with a 10% gelatin solution. The wet granules are screened, dried, mixed with the starch, talc and stearic acid;, screened and compressed into a tablet.

TABLE II

| INGREDIENTS | AMOUNTS |
| --- | --- |
| N-(2-amino-1-benzylethyl)-5-(1-methyl-1H-pyrazol-5-yl)pyrimidine-2-carboxamide (Compound of Example 3) | 20 mg |
| calcium sulfate dehydrate | 30 mg |
| Sucrose | 4 mg |
| Starch | 2 mg |
| Talc | 1 mg |
| stearic acid | 0.5 mg |

While the preferred embodiments of the invention are illustrated by the above, it is to be understood that the invention is not limited to the precise instructions herein disclosed and that the right to all modifications coming within the scope of the following claims is reserved.

What is claimed is:
1. A compound of Formula (I):

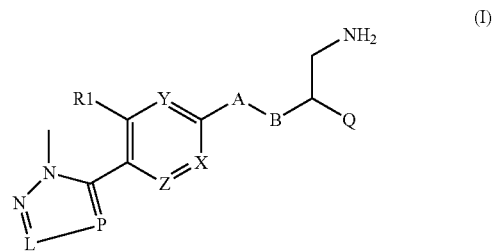

wherein:
Q is selected from: phenyl, substituted phenyl, benzyl, and benzyl wherein the aromatic ring is substituted;
$R^1$ is selected from: hydrogen, trifluoromethyl, hydroxy, —$C_1$-$C_2$alkyl, and halogen;
L is —C(H)—;
P is C($R^{40}$)—, where $R^{40}$ is selected from: hydrogen, —$C_1$-$C_4$alkyl, and halogen;
A is selected from: —C(O)— and —N(H)—;
B is selected from: —C(O)— and —N(H)—; and
X, Y and Z are independently selected from: —C(H)—, and —C($R^2$)—, wherein $R^2$ is selected from halogen, trifluoromethyl, hydroxy, and —$C_1$-$C_4$alkyl;
or a pharmaceutically acceptable salt thereof;
provided:
A and B are not the same.

2. A compound of claim 1 selected from:
N-[2-amino-1-(phenylmethyl)ethyl]-4-(1-methyl-1H-pyrazol-5-yl)benzamide;
N-[2-amino-1-(phenylmethyl)ethyl]-2-chloro-4-(1-methyl-1H-pyrazol-5-yl)benzamide;
N-[2-amino-1-(phenylmethyl)ethyl]-3-chloro-4-(1-methyl-1H-pyrazol-5-yl)benzamide;
N-[2-amino-1-(phenylmethyl)ethyl]-4-(1-methyl-1H-pyrazol-5-yl)-3-(trifluoromethyl)benzamide;
N-((1S)-2-amino-1-{[2-(trifluoromethyl)phenyl]methyl}ethyl)-3-chloro-4-(1-methyl-1H-pyrazol-5-yl)benzamide;
N-[2-amino-1-(phenylmethyl)ethyl]-3-methyl-4-(1-methyl-1H-pyrazol-5-yl)benzamide;
N-((1S)-2-amino-1-{[2-(trifluoromethyl)phenyl]methyl}ethyl)-3-fluoro-4-(1-methyl-1H-pyrazol-5-yl)benzamide;

N-((1S)-2-amino-1-{[2-(trifluoromethyl)phenyl]methyl}ethyl)-3-methyl-4-(1-methyl-1H-pyrazol-5-yl)benzamide;

N-[2-amino-1-(phenylmethyl)ethyl]-3-hydroxy-4-(1-methyl-1H-pyrazol-5-yl)benzamide;

N-[2-amino-1-(phenylmethyl)ethyl]-3-fluoro-4-(1-methyl-1H-pyrazol-5-yl)benzamide;

N-((1S)-2-amino-1-{[2-(trifluoromethyl)phenyl]methyl}ethyl)-4-chloro-5-(1-methyl-1H-pyrazol-5-yl)-2-pyridinecarboxamide;

N-[2-amino-1-(phenylmethyl)ethyl]-4-(4-chloro-1-methyl-1H-pyrazol-5-yl)-3-fluorobenzamide;

N-[2-amino-1-(phenylmethyl)ethyl]-3-chloro-4-(4-chloro-1-methyl-1H-pyrazol-5-yl)benzamide;

N-((1S)-2-amino-1-{[2-(trifluoromethyl)phenyl]methyl}ethyl)-3-fluoro-4-(4-chloro-1-methyl-1H-pyrazol-5-yl)benzamide;

N-((1S)-2-amino-1-{[2-(trifluoromethyl)phenyl]methyl}ethyl)-3-chloro-4-(4-chloro-1-methyl-1H-pyrazol-5-yl)benzamide;

N-[2-amino-1-(phenylmethyl)ethyl]-3-bromo-4-(1-methyl-1H-pyrazol-5-yl)benzamide;

N-((1S)-2-amino-1-{[2-(trifluoromethyl)phenyl]methyl}ethyl)-3-bromo-4-(1-methyl-1H-pyrazol-5-yl)benzamide;

3-amino-N-[3-chloro-4-(1-methyl-1H-pyrazol-5-yl)phenyl]-2-phenylpropanamide; and 3-amino-N-[3-chloro-4-(1-methyl-1H-pyrazol-5-yl)phenyl]-2-(phenylmethyl)propanamide;

or pharmaceutically acceptable salt thereof.

3. A pharmaceutical composition comprising a compound according to claim 1 and a pharmaceutically acceptable carrier.

* * * * *